(12) United States Patent
Cravo et al.

(10) Patent No.: US 9,365,584 B2
(45) Date of Patent: Jun. 14, 2016

(54) THIENO [2,3-B] PYRIDINEDIONE ACTIVATORS OF AMPK AND THERAPEUTIC USES THEREOF

(75) Inventors: Daniel Cravo, Montesson (FR); Sophie Hallakou-Bozec, Montrouge (FR); Sébastien Bolze, Massieux (FR); Franck Lepifre, Saclay (FR); Laurent Faveriel, Longjumeau (FR); Jean-Denis Durand, Montreuil-sous-Bois (FR); Christine Charon, Gometz-le-Chatel (FR)

(73) Assignee: Poxel, Lyons (FR)

( * ) Notice: Subject to any disclaimer, the term of this patent is extended or adjusted under 35 U.S.C. 154(b) by 278 days.

(21) Appl. No.: 13/519,407

(22) PCT Filed: Dec. 28, 2010

(86) PCT No.: PCT/EP2010/070811
§ 371 (c)(1),
(2), (4) Date: Nov. 9, 2012

(87) PCT Pub. No.: WO2011/080277
PCT Pub. Date: Jul. 7, 2011

(65) Prior Publication Data
US 2013/0053401 A1    Feb. 28, 2013

(30) Foreign Application Priority Data

Dec. 29, 2009 (EP) .................................. 09306344

(51) Int. Cl.
*C07D 495/04* (2006.01)
(52) U.S. Cl.
CPC .................................... *C07D 495/04* (2013.01)
(58) Field of Classification Search
CPC .................................................. C07D 495/04
See application file for complete search history.

(56) References Cited

FOREIGN PATENT DOCUMENTS

WO    WO 2009/124636    10/2009

OTHER PUBLICATIONS

Patani et. al. "Bioisosterism: A Rational Approach in Drug Design" Chemical Reviews 1996, 96, 3147-3176.*
Wakefield, Basil "Fluorinated Pharmaceuticals" Innovations in Pharmaceutical Technology 2003, 74, 76-78, Online "http://web.archive.org/web/20030905122408/http://www.iptonline.com/articles/public/IPTFOUR74NP.pdf." (accessed via Wayback machine Nov. 20, 2009 showing web availability as of Sep. 2003).*
Younggil Kwon "Handbook of Essential Pharmacokinetics, Pharmacodynamics and Drug Metabolism for Industrial Scientists" 2001, pp. 47-68.*
International Search Report for PCT/EP2010/070811 mailed Feb. 9, 2011.
Written Opinion of the International Searching Authority mailed Feb. 9, 2011.

* cited by examiner

*Primary Examiner* — David K. O'Dell
(74) *Attorney, Agent, or Firm* — McDonnell Boehnen Hulbert & Berghoff

(57) ABSTRACT

The invention relates to compounds that are direct activators of AMPK (AMP-activated protein kinase) and their use in the treatment of disorders regulated by activation of AMPK. For instance, compounds according to the invention are useful for the treatment of diabetes, metabolic syndrome, obesity, inflammation, cancer and cardiovascular diseases.

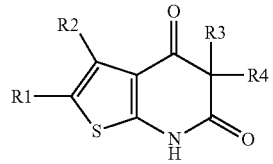

(1)

13 Claims, No Drawings

THIENO [2,3-B] PYRIDINEDIONE ACTIVATORS OF AMPK AND THERAPEUTIC USES THEREOF

This application is the U.S. national phase of International Application No. PCT/EP2010/070811 filed 28 Dec. 2010 which designated the U.S. and claims priority to EP 09306344.4 filed 29 Dec. 2009, the entire contents of each of which are hereby incorporated by reference.

The invention relates to compounds that are direct activators of AMPK (AMP-activated protein kinase) and their use in the treatment of disorders regulated by activation of AMPK. For instance, compounds according to the invention are useful for the treatment of diabetes, metabolic syndrome, obesity, inflammation, cancer and cardiovascular diseases.

BACKGROUND AND INTRODUCTION TO THE INVENTION

AMPK is well established as a sensor and regulator of cellular energy homeostasis (Hardie D. G. and Hawley S. A; "AMP-activated protein kinase: the energy charge hypothesis revisited" Bioassays, 23, 1112, (2001), Kemp B. E. et al. "AMP-activated protein kinase, super metabolic regulator", Biochem; Soc. Transactions, 31, 162 (2003)). Allosteric activation of this kinase due to rising AMP levels occurs in states of cellular energy depletion. The resulting serine/threonine phosphorylation of target enzymes leads to an adaptation of cellular metabolism to low energy state. The net effect of AMPK activation induced changes is inhibition of ATP consuming processes and activation of ATP generating pathways, and therefore regeneration of ATP stores. Examples of AMPK substrates include acetyl-CoA carboxylase (ACC) and HMG-CoA reductase (Carling D. et al. "A common bicyclic protein kinase cascade inactivates the regulatory enzymes of fatty acid and cholesterol biosynthesis", FEBS letters, 223, 217 (1987)). Phosphorylation and therefore inhibition of ACC leads to simultaneous decrease in fatty acid synthesis (ATP-consuming) and increase in fatty acid oxidation (ATP-generating). Phosphorylation and resulting inhibition of HMG-CoA reductase leads to a decrease in cholesterol synthesis. Other substrates of AMPK include hormone sensitive lipase (Garton A. J. et al. "Phosphorylation of bovine hormone-sensitive lipase by AMP-activated protein kinase; A possible antilipolytic mechanism", Eur. J. Biochem. 179, 249, (1989)), glycerol-3-phosphate acyltransferase (Muoio D. M. et al. "AMP-activated kinase reciprocally regulates triacylglycerol synthesis and fatty acid oxidation in liver and muscle: evidence that sn-glycerol-3-phosphate acyltransferase is a novel target", Biochem. J., 338, 783, (1999)), malonyl-CoA decarboxylase (Sarah A. K. et al. "Activation of malonyl-CoA decarboxylase in rat skeletal muscle by contraction and the AMP-activated protein kinase activator 5-aminoimidazole-4-caboxamide-1-beta-D-ribofuranoside", J. Biol. Chem. 275, 24279, (2000)).

AMPK is also involved in the regulation of liver metabolism. Elevated glucose production by the liver is a major cause of fasting hyperglycemia in type 2 diabetes (T2D) (Saltiel et al. "New perspectives into the molecular pathogenesis and treatment of type 2 diabetes", Cell 10, 517-529 (2001)). Gluconeogenesis in the liver is regulated by multiple enzymes such as phosphoenolpyruvate carboxykinase (PEPCK) and glucose-6-phosphatase -G6Pase. Activation of AMPK suppresses the transcription of theses genes in hepatoma cells (Lochhead et al. "5-aminoimidazole-4-carboxamide riboside mimics the effects of insulin on the expression of the 2 key gluconeogenic genes PEPCK and glucose-6-phosphatase", Diabetes, 49, 896-903 (2000)).

AMPK activation also down-regulates gluconeogenesis acting on some other genes expression. These effects may be due to its ability to down-regulate key transcription factors such as SREBP-1c (Zhou G. et al., "Role of AMP-activated protein kinase in mechanism of metformin action" J. Clin. Invest., 108, 1167 (2001)), ChREBP (Kawaguchi T. et al., "Mechanism for fatty acids sparing effect on glucose induced transcription: regulation of carbohydrate response element binding protein by AMP-activated protein kinase" J. Biol. Chem. 277, 3829 (2001)), or HNF-4-alpha (Leclerc I. et al., "Hepatocyte nuclear factor-4alpha involved in type 1 maturity-onset diabetes of the young is a novel target of AMP-activated protein kinase" Diabetes, 50, 1515 (2001)) or to direct phosphorylate transcriptional coactivators such as p300 (Yang W et al., "Regulation of transcription by AMP-activated protein kinase; Phosphorylation of p300 blocks its interaction with nuclear receptors" J. Biol. Chem. 276, 38341 (2001)) or TORC2.

AMPK is considered as an attractive candidate for contraction-induced skeletal muscle glucose uptake because it is activated in parallel with elevation in AMP and a reduction in creatine phosphate energy stores (Hutber et al. "Electrical stimulation inactivates muscle acetyl-CoA carboxylase and increases AMP-activated protein kinase" Am. J. Physiol. Endocrinol. Metab. 272, E262-E66 (1997)). Furthermore, AICAR-induced activation of AMPK increases glucose uptake (Merrill et al. "AICA Riboside increases AMP-activated protein kinase, fatty acid oxidation and glucose uptake in rat muscle" Am. J. Physiol. Endocrinol. Metab. 273, E1107-E1112 (1997)) concomitantly with glucose transporter 4 (GLUT4) fusion with plasma membrane (Kurth-Kraczek "5'-AMP-activated protein kinase activation causes GLUT4 translocation in skeletal muscle", Diabetes, 48, 1667-1671 (1999)). Over-expression of an alpha2 kinase dead subunit in skeletal muscle abolishes AICAR, but partially impairs contraction-stimulated glucose uptake (Mu J. et al. "A role for AMP-activated protein kinase in contraction and hypoxia-regulated glucose transport in skeletal muscle", Mol. Cell. 7, 1085-1094 (2001)). These findings suggest that additional pathways mediate contraction induced glucose uptake, whereas it is clear that AMPK mediates the effects of AICAR on glucose uptake.

Despite extensive studies on upstream stimuli that activate AMPK, investigation on the downstream substrate(s) of AMPK-mediated glucose uptake is lacking. More recent reports revealed that Akt substrate of 160 kDa (AS160) is an important substrate downstream of Akt that is involved in insulin-stimulated glucose uptake. In addition to insulin, contraction and activation of AMPK by AICAR is associated with increased phosphorylation of AS160 in rodent skeletal muscle. Phosphorylation of AS160 is impaired or abolished in skeletal muscle from AMPK a2 knockout, g3 knockout, and a2-kinase dead mice in response to AICAR treatment (Treeback et al. "AMPK-mediated AS160 phosphorylation in skeletal muscle is dependent on AMPK catalytic and regulatory subunits", Diabetes (2006)). This corroborates findings of impaired AICAR-stimulated glucose uptake in skeletal muscle of such mice (Jorgensen S. B. et al. "Knockout of the a2 but not a1 5'-AMP-activated protein kinase isoform abolishes 5-aminoimidazole-4-carboxamide-1b-4 ribofuranoside but not contraction-induced glucose uptake in skeletal muscle", J. Biol. Chem. 279, 1070-1079 (2004)). Therefore, AS160 appears to be a downstream target of AMPK in mediating glucose uptake in skeletal muscle.

Taken together, all these metabolic effects evidence that AMPK suppresses liver gluconeogenesis and lipid production, while decreasing hepatic lipid deposition via increased lipid oxidation, thus improving the glucose and lipid profiles in T2D. More recently, involvement of AMPK in the regulation of not only cellular but also whole body energy metabolism has become apparent. It was shown that the adipocyte-derived hormone leptin leads to a stimulation of AMPK and therefore to an increase in fatty acid oxidation in skeletal muscle (Minokoshi Y. et al. "Leptin stimulates fatty-acid oxidation by activating AMP activated protein kinase", Nature, 415, 339 (2002)). Adiponectin, another adipocyte derived hormone leading to improved carbohydrate and lipid metabolism, has been shown to stimulate AMPK liver and skeletal muscles (Yamanauchi T. et al. "Adiponectin stimulates glucose utilization and fatty acid oxidation by activating AMP-activated protein kinase", Nature Medicine, 8, 1288, (2002), Tomas E. et al. "Enhanced muscle fat oxidation and glucose transport by ACRP30 globular domain: Acetyl-CoA carboxylase inhibition and AMP-activated protein kinase activation" PNAS, 99, 16309, (2002)). The activation of AMPK in these circumstances seems independent of increasing cellular AMP levels but rather due to phosphorylation by one or more upstream kinases yet to be identified.

Based on the knowledge of the above-mentioned consequences of AMPK activation, deep beneficial effects would be expected from in vivo activation of AMPK. In liver, decreased expression of gluconeogenic enzymes would be expected to reduce hepatic glucose output and improve overall glucose homeostasis; both direct inhibition and/or reduced expression of key enzymes in lipid metabolism would be expected to increase glucose uptake and fatty acid oxidation with resulting improvement of glucose homeostasis and, due to a reduction in intra-myocyte triglyceride accumulation, to improved insulin action. Finally, the increase in energy expenditure should lead to a decrease in body weight. The combination of these effects in the metabolic syndrome would be expected to significantly reduce the risk of developing cardiovascular diseases. Several studies in rodents support this hypothesis (Bergeron R. et al. "Effect of 5-aminoimidazole-4-carboxamide-1(beta)-D-rifuranoside infusion on in vivo glucose metabolism in lean and obese Zucker rats", Diabetes, 50, 1076 (2001), Song S. M. et al. "5-aminoimidazole-4-dicarboxamide ribonucleoside treatment improves glucose homeostasis in insulin-resistant diabeted (ob/ob) mice", Diabetologia, 45, 56 (2002), Halseth A. E. et al. "Acute and chronic treatment of ob/ob and db/db mice with AICAR decreases blood glucose concentrations", Biochem. and Biophys. Res. Comm., 294, 798 (2002), Buhl E. S. et al. "Long-term AICAR administration reduces metabolic disturbances and lowers blood pressure in rats displaying feature of the insulin resistance syndrome", Diabetes, 51, 2199 (2002)). Until recently, most in vivo studies relied on AICAR AMPK activator, a cell permeable precursor of ZMP. ZMP, a structural analogue of AMP, acts as an intracellular AMP mimic and, when accumulated to high enough levels, is able to stimulate AMPK activity (Corton J. M. et al. "5-aminoimidazole-4-dicarboxamide ribonucleoside, a specific method for activating AMP-activated protein kinase in intact cells?", Eur. J. Biochem., 229, 558 (1995)). However, ZMP also acts as an AMP mimic in the regulation of other enzymes, and is therefore not a specific AMPK activator (Musi N. and Goodyear L. J., "Targeting the AMP-activated protein kinase for the treatment of type 2 diabetes", Current Drug Targets-immune, Endocrine and Metabolic Disorders, 2 119 (2002)). Several in vivo studies have demonstrated beneficial effects of both acute and chronic AICAR administrations in rodent models of obesity and type 2 diabetes (Bergeron R. et al. "Effect of 5-aminoimidazole-4-carboximide-1b-D ribofuranoside infusion on in vivo glucose metabolism in lean and obese Zucker rats", Diabetes, 50, 1076, (2001), Song S. M. et al. "5-aminoimidazole-4-carboxamide ribonucleotide treatment improves glucose homeostasis in insulin resistant diabetic (ob/bo) mice", Diabetologia, 45, 56, (2002), Halseth A. E. et al. "Acute and chronic treatment of ob/ob and db/db mice with AICAR decreases blood glucose concentrations" Biochem. Biophys. Res. Comm. 294, 798, (2002), Buhl E. S. et al. "Long-term AICAR administration reduces metabolic disturbances and lowers blood pressure in rats displaying feature of the insulin resistance syndrome", Diabetes, 51, 2199 (2002)). For example, 7 week AICAR administration in the obese Zucker (fa/fa) rat leads to a reduction in plasma triglycerides and free fatty acids, an increase in HDL cholesterol, and a normalisation of glucose metabolism as assessed by an oral glucose tolerance test (Minokoshi Y. et al. "Leptin stimulates fatty-acid oxidation by activating AMP-activated protein kinase", Nature, 415, 339, -2002)). In both ob/ob and db/db mice, 8 day AICAR administration reduces blood glucose by 35% (Halseth A. E. et al. "Acute and chronic treatment of ob/ob and db/db mice with AICAR decreases blood glucose concentrations", Biochem. Biophys. Res. Comm., 294, 798 (2002)). In addition to AICAR, it was found that the diabetes drug metformin can activate AMPK in vivo at high concentrations (Zhou G. et al. "Role of AMP-activated protein kinase in mechanism of metformin action", J. Clin. Invest., 108, 1167, (2001), Musi N. et al. "Metformin increases AMP-activated protein kinase activity in skeletal muscle of subjects with type 2 diabetes", Diabetes, 51, 2074, (2002)), although it has to be determined to what extent its antidiabetic action relies on this activation. As with leptin and adiponectin, the stimulatory effect of metformin is indirect via activation of an upstream kinase (Zhou G. et al. "Role of AMP-activated protein kinase in mechanism of metformin action", J. Clin. Invest., 108, 1167, (2001)). More recently, a small molecule AMPK activator has been described. This direct AMPK activator, named A-769662, is a thienopyridone and induces in vivo a decrease in plasma levels of glucose and triglycerides (Cool B. et al. "Identification and characterization of a small molecule AMPK activator that treats key components of type 2 diabetes and the metabolic syndrome", Cell Metab., 3, 403-416, (2006)).

In addition to pharmacological intervention, several transgenic mice models have been developed in the last years, and initial results are currently becoming available. Expression of dominant negative AMPK in skeletal muscle of transgenic mice demonstrated the effect of AICAR on stimulation of glucose transport is dependent on AMPK activation (Mu J. et al. "Role for AMP-activated protein kinase in contraction and hypoxia regulated glucose transport in skeletal muscle", Molecular Cell, 7, 1085, (2001)), and therefore likely not caused by non-specific ZMP effects. Similar studies in other tissues will help to further define the consequences of AMPK activation. It is expected that pharmacological activation of AMPK will have benefits in the metabolic syndrome with improved glucose and lipid metabolisms and reduction in body weight. In order to qualify a patient as having metabolic syndrome, three out of the five following criteria must be met:

1) elevated blood pressure (above 130/85 mmHg),
2) fasting blood glucose above 110 mg/dl,
3) abdominal obesity above 40" (men) or 35" (women) waist circumference, and blood lipid changes as defined by
4) increase in triglycerides above 150 mg/dl, or
5) decrease in HDL cholesterol below 40 mg/dl (men) or 50 mg/dl (women).

Therefore, the combined effects that may be achieved through activation of AMPK in a patient who is qualified as having metabolic syndrome would raise the interest of this target.

Stimulation of AMPK has been shown to stimulate expression of uncoupling protein 3 (UCP3) skeletal muscle (Zhou M. et al. "UCP-3 expression in skeletal muscle: effects of exercise, hypoxia, and AMP-activated protein kinase", Am. J. Physiol. Endocrinol. Metab., 279, E622, (2000)) and might therefore be a way to prevent from damage from reactive oxygen species. Endothelial NO synthase (eNOS) has been shown to be activated through AMPK mediated phosphorylation (Chen Z.-P. et al. "AMP-activated protein kinase phosphorylation of endothelial NO synthase", FEBS Letters, 443, 285, (1999)), therefore AMPK activation can be used to improve local circulatory systems.

AMPK has a role in regulating the mTOR pathway. mTOR is a serine/threonine kinase and is a key regulator of protein synthesis. To inhibit cell growth and protect cells from apoptosis induced by glucose starvation, AMPK phosphorylates TSC2 at Thr-1227 and Ser-1345, increasing the activity of the TSC1 and TSC-2 complexes to inhibit m-TOR. In addition, AMPK inhibits mTOR action by phosphorylation on Thr-2446. Thus, AMPK indirectly and directly inhibits the activity of mTOR to limit protein synthesis. AMPK may also be a therapeutic target for many cancers that have constitutive activation of the PI3K-Akt signalling pathway. Treatment of various cancer cell lines by AICAR attenuated the cell proliferation both in in vitro and in vivo studies (Giri R., "5-Aminoimidazole-4-carboxamide-1-beta-4-ribofuranoside inhibits cancer cell proliferation in vitro and in vivo via AMP-activated protein kinase (AMPK)", J. Biol. Chem. (2005)). Two reports link the treatment with metformin with a lower risk of cancer in diabetic patients (Evans J. M. "Metformin and reduced risk of cancer in diabetic patients", BMJ, 330, 1304-1305, (2005)).

Activation of AMPK by AICAR has been shown to reduce expression of the lipogenic enzymes FAS and ACC, resulting in suppression of proliferation in prostate cancer cells. Many cancer cells display a markedly increased rate of de novo fatty acid synthesis correlated with high levels of FAS. Inhibition of FAS suppresses cancer cell proliferation and induces cell death. Thus, AMPK activation and inhibition of FAS activity is a clear target for pharmacological therapy of cancers.

In some publications it has been described that AICAR as an AMPK activator exerts anti-inflammatory diseases. It has been observed that AICAR attenuates the production of proinflammatory cytokines and mediators (S. Giri et al. J. Neuroscience 2004, 24:479-487), AICAR in rat model and in vitro attenuates EAE progression by limiting infiltration of leucocytes across blood brain barrier (BBB) (Nath. N. et al. J. of Immunology 2005, 175:566-574; Prasad R. et al. J. Neurosci Res. 2006, 84:614-625) and it has been suggested recently that AMPK activating agents act as anti-inflammatory agents and can hold a therapeutic potential in Krabbe disease/twitcher disease (an inherited neurological disorder) (S. Giri et al. J. Neurochem. 2008, Mar. 19).

DESCRIPTION OF THE INVENTION

The present invention discloses compounds of formula (1):

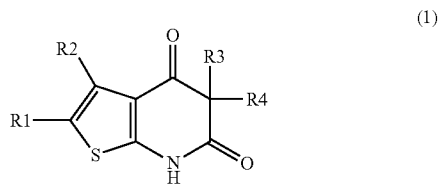

wherein
R1 represents a hydrogen atom, an alkyl group or a halogen atom;
R2 represents an aryl or heteroaryl group;
R3 and R4 independently represent a halogen atom, an alkyl, aryl, cycloalkyl, heterocycloalkyl, alkyloxy, cyano (CN), aralkyl, heteroaryl, CO2R5 (carboxy or alkyloxycarbonyl) or CONR6R7 (carboxamide, mono- or di-alkylaminocarbonyl) group;
R5, R6 and R7 independently represent a hydrogen atom or an alkyl group;
R6 and R7 can alternatively be fused to form a cycle containing the nitrogen atom.

Compounds of formula (1) also include their geometric isomers, tautomers, epimers, enantiomers, stereoisomers, diastereoisomers, racemates, pharmaceutically acceptable salts, prodrugs, solvates, and mixtures thereof in all ratios.

Compounds of formula (1) are direct AMPK activators.

Compounds of formula (1) are useful for the treatment of diseases for which AMPK activation has a positive effect onto subject health. Among diseases for which treatment with compounds of formula (1) is suitable may be cited diabetes, metabolic syndrome, obesity, inflammation, cancer and cardiovascular diseases.

In accordance with the present invention and as used herein, the following terms are defined with the following meanings unless explicitly stated otherwise.

The term "alkyl group" refers to a linear or branched saturated chain of 1 to 5 carbon atoms, such as methyl, ethyl, n-propyl, iso-propyl, n-butyl, sec-butyl, iso-butyl or tert-butyl. Preferably, alkyl groups are linear or branched saturated chains of 1 to 3 carbon atoms, such as methyl, ethyl, n-propyl, iso-propyl group.

A "cycloalkyl group" is intended to mean a saturated non-aromatic, monovalent monocyclic, bicyclic, or tricyclic radical containing 3, 4, 5, 6, 7, 8, 9, 10, 11, 12, 13, or 14 carbon ring atoms, and which may be unsubstituted or substituted by one or more atoms or groups selected among halogen atoms, alkyl groups, hydroxy (OH), alkyloxy groups, aralkyloxy groups, amino (NH2), mono- or di-alkylamino groups, carboxy (COOH), alkyloxycarbonyl groups, mono- or di-alkylaminocarbonyl groups, carboxamide (CONH2), cyano (CN), alkylsulfonyl groups and trifluoromethyl (CF3). Illustrative examples of cycloalkyl groups include, but are not limited to, cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]nonyl, bicyclo[4.3.0]nonyl, bicyclo[4.4.0]decyl, adamantyl, and the like.

A "heterocycloalkyl group" is intended to mean a saturated, non-aromatic, monovalent monocyclic, bicyclic, or tricyclic radical, containing 3, 4, 5, 6, 7, 8, 9, 10, 11, 12, 13, 14, 15, 16, 17, or 18 ring atoms, and which includes 1, 2, 3, 4, or 5 heteroatoms selected from nitrogen, oxygen and sulphur, wherein the group is unsubstituted or substituted by one or more atoms or groups selected among halogen atoms, alkyl groups, hydroxy (OH), alkyloxy groups, aralkyloxy groups, amino (NH2), mono- or di-alkylamino groups, carboxy (COOH), alkyloxycarbonyl groups, mono- or di-alkylaminocarbonyl groups, carboxamide (CONH2), cyano (CN), alkylsulfonyl groups and trifluoromethyl (CF3). Illustrative examples of heterocycloalkyl groups include, but are not limited to, azetidinyl, pyrrolidyl, piperidyl, piperazinyl, morpholinyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3.3.1]nonyl, azabicylo[4.3.0]nonyl, oxabicylo[2.2.1]heptyl, 1,5,9-triazacyclododecyl, and the like.

The term "aryl group" refers to an aromatic group like phenyl or naphthyl group, optionally substituted by one or more atoms or groups selected among halogen atoms, alkyl groups, hydroxy (OH), alkyloxy groups, aralkyloxy groups, amino (NH2), mono- or di-alkylamino groups, carboxy (COOH), alkyloxycarbonyl groups, mono- or di-alkylaminocarbonyl groups, carboxamide (CONH2), cyano (CN), alkylsulfonyl groups and trifluoromethyl (CF3). More specifically, the aryl group can be substituted or not by fluorine, chlorine, bromine atoms, hydroxy, methoxy, ethoxy, benzyloxy, amino, dimethylamino, diethylamino, methyl, ethyl, n-propyl, n-butyl, iso-propyl, sec-butyl, iso-butyl, tert-butyl, carboxy, methoxycarbonyl, ethoxycarbonyl, carboxamide, dimethylaminocarbonyl, methylaminocarbonyl, cyano, methylsulfonyl, or trifluoromethyl group.

The term "alkyloxy group" or "aralkyloxy group" respectively refers to an alkyl or aralkyl group linked to the rest of the molecule through an oxygen atom. Among alkyloxy and aralkyloxy groups can be more specifically cited methoxy, ethoxy and benzyloxy groups. The term "alkylamino group" refers to an alkyl group linked to the rest of the molecule through a nitrogen atom. Among alkylamino groups can be cited dimethylamino and diethylamino groups.

The term "alkylsulfonyl" refers to an alkyl linked to the rest of the molecule through a SO2 group. Among alkylsulfonyl groups can be cited methylsulfonyl and ethylsulfonyl groups.

The term "halogen atom" refers to an atom selected from fluorine, chlorine, bromine and iodine atoms.

The term "heteroaryl group" refers to an aromatic group including one or more heteroatoms selected from nitrogen, oxygen and sulphur. Among heteroaryl groups can be cited pyridine, pyrazine, pyrimidine, thiophene, furan, isoxazole, isothiazole, pyrazole, imidazole. Such groups may be substituted by atoms or groups selected from halogen atoms, alkyl groups, hydroxy (OH), alkyloxy groups, aralkyloxy groups, amino (NH2), mono- or di-alkylamino groups, carboxy (COOH), alkyloxycarbonyl groups, mono- or di-alkylaminocarbonyl groups, carboxamide (CONH2), cyano (CN), alkylsulfonyl groups and trifluoromethyl (CF3). More specifically, the heteroaryl group can be substituted or not by fluorine, chlorine, bromine atoms, hydroxy, methoxy, ethoxy, benzyloxy, amino, dimethylamino, diethylamino, methyl, ethyl, n-propyl, n-butyl, iso-propyl, sec-butyl, iso-butyl, tert-butyl, carboxy, methoxycarbonyl, ethoxycarbonyl, carboxamide, dimethylaminocarbonyl, methylaminocarbonyl, cyano, methylsulfonyl, or trifluoromethyl group.

The term "aralkyl group" refers to an alkyl group substituted with an aryl group. Among aralkyl groups can be cited benzyl and phenethyl groups. Aralkyl groups may be substituted by atoms or groups selected from halogen atoms, alkyl groups, hydroxy (OH), alkyloxy groups, aralkyloxy groups, amino (NH2), mono- or di-alkylamino groups, carboxy (COOH), alkyloxycarbonyl groups, mono- or di-alkylaminocarbonyl groups, carboxamide (CONH2), cyano (CN), alkylsulfonyl groups and trifluoromethyl (CF3). More specifically, the aralkyl group can be substituted or not by fluorine, chlorine, bromine atoms, hydroxy, methoxy, ethoxy, benzyloxy, amino, dimethylamino, diethylamino, methyl, ethyl, n-propyl, n-butyl, iso-propyl, sec-butyl, iso-butyl, tert-butyl, carboxy, methoxycarbonyl, ethoxycarbonyl, carboxamide, dimethylaminocarbonyl, methylaminocarbonyl, cyano, methylsulfonyl, or trifluoromethyl group.

When R6 and R7 are fused to form a cycle containing the nitrogen atom, the cycle can be any type of heterocycloalkyl and heteroaryl as defined above and containing at least one nitrogen atom as heteroatom. One can cite for instance azetidine, pyrrolidine, piperidine, or azepine group.

"Solvates" of the compounds are taken in the present invention to mean adductions of inert solvent molecules onto the compounds which form owing to their mutual attractive force. Solvates are, for example, mono- or dihydrates or alcoholates.

A particular object of the present invention is a compound of formula (1), wherein R3 represents a halogen atom, preferably fluorine or chlorine, more preferably fluorine.

Another particular object of the present invention is a compound of formula (1), wherein R3 represents an alkyl group, preferably a methyl group.

Another particular object of the present invention is a compound of formula (1), wherein R1 represents a halogen atom, preferably fluorine or chlorine, more preferably.

Another particular object of the present invention is a compound of formula (1), wherein R1 represents an alkyl group, preferably a methyl group.

Another particular object of the present invention is a compound of formula (1), wherein R2 represents an aryl group, substituted or not by one or more (2, 3, 4 or 5) atoms or groups selected among halogen atoms, alkyl groups, hydroxyl groups, alkoxy groups, aralkyloxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups, more preferably substituted by one or more (2, 3, 4 or 5) atoms or groups selected among halogen atoms, alkyl groups, hydroxyl groups, alkoxy groups, and aralkyloxy groups, Another particular object of the present invention is a compound of formula (1), wherein R4 represents an aryl or heteroaryl group, substituted or not by one or more (2, 3, 4 or 5) atoms or groups selected among halogen atoms, alkyl groups, hydroxyl groups, alkoxy groups, aralkyloxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups.

Any combination (whenever possible) of the above described particular objects corresponds to preferred embodiments of the inventive compounds.

The invention additionally relates to crystalline and polymorphic forms of compounds of formula (1) and derivatives described above.

The present invention is directed not only to racemic mixtures of these compounds, but also to individual stereoisomers and/or diastereoisomers thereof as well or as mixtures of these in all proportions.

The term "prodrug" as used herein refers to any compound that when administered to a biological system generates the "drug" substance (a biologically active compound) as a result of spontaneous chemical reaction(s), enzyme catalyzed chemical reaction(s), and/or metabolic chemical reaction(s). This also includes biodegradable polymer derivatives of the compounds according to the invention, as is described, for example, in Int. J. Pharm. 115, 61-67 (1995).

Some preferred compounds of formula (1) are the following:

5-methyl-3,5-diphenyl-7H-thieno[2,3-b]pyridine-4,6-dione
2-chloro-5-methyl-3,5-diphenyl-7H-thieno[2,3-b]pyridine-4,6-dione
2-chloro-3-(2-fluoro-4-methoxy-phenyl)-5-methyl-5-phenyl-7H-thieno[2,3-b]pyridine-4,6-dione
3-(3-fluoro-2-methoxy-4-methyl-phenyl)-5-methyl-5-(p-tolyl)-7H-thieno[2,3-b]pyridine-4,6-dione
2-chloro-3-(3-fluoro-2-methoxy-4-methyl-phenyl)-5-methyl-5-phenyl-7H-thieno[2,3-b]pyridine-4,6-dione
2-chloro-3-(4-fluoro-2-methoxy-phenyl)-5-methyl-5-phenyl-7H-thieno[2,3-b]pyridine-4,6-dione
2-chloro-3-(1-hydroxy-2-naphthyl)-5-methyl-5-phenyl-7H-thieno[2,3-b]pyridine-4,6-dione
3-(1-hydroxy-2-naphthyl)-5-methyl-5-phenyl-7H-thieno[2,3-b]pyridine-4,6-dione
3,5,5-triphenyl-7H-thieno[2,3-b]pyridine-4,6-dione
5-benzyl-3,5-diphenyl-7H-thieno[2,3-b]pyridine-4,6-dione
5-ethyl-3,5-diphenyl-7H-thieno[2,3-b]pyridine-4,6-dione
2-chloro-3-(3-ethoxy-4-fluoro-2-methoxy-phenyl)-5-methyl-5-phenyl-7H-thieno[2,3-b]pyridine-4,6-dione
2-chloro-3-(3,4-difluoro-2-methoxy-phenyl)-5-methyl-5-phenyl-7H-thieno[2,3-b]pyridine-4,6-dione
3-(3,4-difluoro-2-hydroxy-phenyl)-5-methyl-5-phenyl-7H-thieno[2,3-b]pyridine-4,6-dione
2-chloro-3-(4-fluoro-2-hydroxy-phenyl)-5-(4-methoxyphenyl)-5-methyl-7H-thieno[2,3-b]pyridine-4,6-dione
3-(4-ethyl-2-methoxy-phenyl)-5-methyl-5-phenyl-7H-thieno[2,3-b]pyridine-4,6-dione
5-(4-ethoxyphenyl)-3-(2-fluoro-4-methyl-phenyl)-5-methyl-7H-thieno[2,3-b]pyridine-4,6-dione
5,5-dimethyl-3-phenyl-7H-thieno[2,3-b]pyridine-4,6-dione
5-(4-ethoxyphenyl)-3-(4-fluoro-2-hydroxy-3-methyl-phenyl)-2,5-dimethyl-7H-thieno[2,3-b]pyridine-4,6-dione
2-chloro-5-fluoro-3,5-diphenyl-7H-thieno[2,3-b]pyridine-4,6-dione
3-(4-chloro-2-methoxy-phenyl)-5-(4-ethoxyphenyl)-5-methyl-7H-thieno[2,3-b]pyridine-4,6-dione
2-chloro-5-(4-ethoxyphenyl)-3-(2-fluoro-4-methyl-phenyl)-5-methyl-7H-thieno[2,3-b]pyridine-4,6-dione
5-(4-ethoxyphenyl)-3-(3-fluoro-2-hydroxy-4-methyl-phenyl)-5-methyl-7H-thieno[2,3-b]pyridine-4,6-dione
3-(3-fluoro-2-hydroxy-4-methyl-phenyl)-5-(4-hydroxyphenyl)-5-methyl-7H-thieno[2,3-b]pyridine-4,6-dione
5-fluoro-3-(4-fluoro-2-hydroxy-phenyl)-5-phenyl-7H-thieno[2,3-b]pyridine-4,6-dione
2-chloro-3-(4-fluorophenyl)-5-methyl-5-phenyl-7H-thieno[2,3-b]pyridine-4,6-dione
2-chloro-5-(3-fluorophenyl)-5-methyl-3-phenyl-7H-thieno[2,3-b]pyridine-4,6-dione
2-chloro-5-(2-fluorophenyl)-5-methyl-3-phenyl-7H-thieno[2,3-b]pyridine-4,6-dione
2-chloro-3-(3-fluorophenyl)-5-methyl-5-phenyl-7H-thieno[2,3-b]pyridine-4,6-dione
2-chloro-3-(2-fluorophenyl)-5-methyl-5-phenyl-7H-thieno[2,3-b]pyridine-4,6-dione
2-chloro-5-methyl-3-phenyl-5-(p-tolyl)-7H-thieno[2,3-b]pyridine-4,6-dione
2-chloro-5-(4-fluorophenyl)-5-methyl-3-phenyl-7H-thieno[2,3-b]pyridine-4,6-dione
2-chloro-5-methyl-5-(m-tolyl)-3-phenyl-7H-thieno[2,3-b]pyridine-4,6-dione
2-chloro-5-methyl-5-phenyl-3-(p-tolyl)-7H-thieno[2,3-b]pyridine-4,6-dione
2-chloro-5-(4-methoxyphenyl)-5-methyl-3-phenyl-7H-thieno[2,3-b]pyridine-4,6-dione
2-chloro-3-(4-methoxyphenyl)-5-methyl-5-phenyl-7H-thieno[2,3-b]pyridine-4,6-dione
2-chloro-3-(3-fluorophenyl)-5-(4-fluorophenyl)-5-methyl-7H-thieno[2,3-b]pyridine-4,6-dione
2-chloro-5-(3-methoxyphenyl)-5-methyl-3-phenyl-7H-thieno[2,3-b]pyridine-4,6-dione
2-chloro-5-(4-fluorophenyl)-3-(4-methoxyphenyl)-5-methyl-7H-thieno[2,3-b]pyridine-4,6-dione
2-chloro-3-(3-methoxyphenyl)-5-methyl-5-phenyl-7H-thieno[2,3-b]pyridine-4,6-dione
2-chloro-3-(3-methoxyphenyl)-5-methyl-5-(p-tolyl)-7H-thieno[2,3-b]pyridine-4,6-dione
2-chloro-5-(4-fluorophenyl)-3-(3-methoxyphenyl)-5-methyl-7H-thieno[2,3-b]pyridine-4,6-dione
2-chloro-3-(3-methoxyphenyl)-5-(4-methoxyphenyl)-5-methyl-7H-thieno[2,3-b]pyridine-4,6-dione
2-chloro-3-(3-methoxyphenyl)-5-methyl-5-(m-tolyl)-7H-thieno[2,3-b]pyridine-4,6-dione
2-chloro-5-(3-fluorophenyl)-5-methyl-3-(p-tolyl)-7H-thieno[2,3-b]pyridine-4,6-dione
2-chloro-5-fluoro-3-(4-fluoro-2-hydroxy-phenyl)-5-phenyl-7H-thieno[2,3-b]pyridine-4,6-dione
2-chloro-5-(2-fluorophenyl)-5-methyl-3-(o-tolyl)-7H-thieno[2,3-b]pyridine-4,6-dione
2-chloro-5-methoxy-3,5-diphenyl-7H-thieno[2,3-b]pyridine-4,6-dione
2-chloro-3,5-bis(4-fluorophenyl)-5-methyl-7H-thieno[2,3-b]pyridine-4,6-dione
2-chloro-3-(4-fluorophenyl)-5-methyl-5-(p-tolyl)-7H-thieno[2,3-b]pyridine-4,6-dione
2-chloro-5-(3-fluorophenyl)-3-(4-fluorophenyl)-5-methyl-7H-thieno[2,3-b]pyridine-4,6-dione
2-chloro-5-(4-fluorophenyl)-3-(2-methoxyphenyl)-5-methyl-7H-thieno[2,3-b]pyridine-4,6-dione
2-chloro-3-(4-fluorophenyl)-5-(4-methoxyphenyl)-5-methyl-7H-thieno[2,3-b]pyridine-4,6-dione
2-chloro-3-(4-fluorophenyl)-5-methyl-5-(4-methylsulfonylphenyl)-7H-thieno[2,3-b]pyridine-4,6-dione
2-chloro-5-(2-fluorophenyl)-3-(4-fluorophenyl)-5-methyl-7H-thieno[2,3-b]pyridine-4,6-dione
2-chloro-3-(2-methoxyphenyl)-5-methyl-5-(m-tolyl)-7H-thieno[2,3-b]pyridine-4,6-dione
2-chloro-5-(4-fluorophenyl)-5-methyl-3-(p-tolyl)-7H-thieno[2,3-b]pyridine-4,6-dione
2-chloro-5-(3-methoxyphenyl)-5-methyl-3-(o-tolyl)-7H-thieno[2,3-b]pyridine-4,6-dione
2-chloro-5-methyl-5-(m-tolyl)-3-(o-tolyl)-7H-thieno[2,3-b]pyridine-4,6-dione
2-chloro-3-(3-fluorophenyl)-5-methyl-5-(p-tolyl)-7H-thieno[2,3-b]pyridine-4,6-dione
2-chloro-3,5-bis(3-methoxyphenyl)-5-methyl-7H-thieno[2,3-b]pyridine-4,6-dione
2-chloro-5-(3-fluorophenyl)-3-(3-methoxyphenyl)-5-methyl-7H-thieno[2,3-b]pyridine-4,6-dione
2-chloro-3-(4-fluorophenyl)-5-(3-methoxyphenyl)-5-methyl-7H-thieno[2,3-b]pyridine-4,6-dione
2-chloro-3-(4-fluorophenyl)-5-methyl-5-(3-methylsulfonylphenyl)-7H-thieno[2,3-b]pyridine-4,6-dione
2-chloro-3-(2-methoxyphenyl)-5-methyl-5-(p-tolyl)-7H-thieno[2,3-b]pyridine-4,6-dione
2-chloro-5-(3-fluorophenyl)-3-(2-methoxyphenyl)-5-methyl-7H-thieno[2,3-b]pyridine-4,6-dione
2-chloro-3-(2-methoxyphenyl)-5-(4-methoxyphenyl)-5-methyl-7H-thieno[2,3-b]pyridine-4,6-dione 2-chloro-3-(2-methoxyphenyl)-5-(3-methoxyphenyl)-5-methyl-7H-thieno[2,3-b]pyridine-4,6-dione
2-chloro-5-(2-fluorophenyl)-3-(2-methoxyphenyl)-5-methyl-7H-thieno[2,3-b]pyridine-4,6-dione
5-fluoro-2-methyl-3,5-diphenyl-7H-thieno[2,3-b]pyridine-4,6-dione
2-chloro-5-fluoro-5-phenyl-3-(3-pyridyl)-7H-thieno[2,3-b]pyridine-4,6-dione
2-chloro-5-fluoro-3-(4-hydroxyphenyl)-5-phenyl-7H-thieno[2,3-b]pyridine-4,6-dione
2-chloro-5-fluoro-3-(2-fluorophenyl)-5-phenyl-7H-thieno[2,3-b]pyridine-4,6-dione
2-chloro-5-fluoro-3-(2-fluoro-4-methoxy-phenyl)-5-phenyl-7H-thieno[2,3-b]pyridine-4,6-dione
2-chloro-3-(2-fluorophenyl)-5-methyl-5-(p-tolyl)-7H-thieno[2,3-b]pyridine-4,6-dione
2-chloro-3-(2-fluorophenyl)-5-(3-methoxyphenyl)-5-methyl-7H-thieno[2,3-b]pyridine-4,6-dione
2-chloro-5-fluoro-3-(3-fluoro-4-hydroxyphenyl)-5-phenyl-7H-thieno[2,3-b]pyridine-4,6-dione
5-fluoro-5-(2-methoxyphenyl)-2-methyl-3-phenyl-7H-thieno[2,3-b]pyridine-4,6-dione
2-chloro-5-fluoro-3-(m-tolyl)-5-phenyl-7H-thieno[2,3-b]pyridine-4,6-dione
2-chloro-5-fluoro-5-phenyl-3-(p-tolyl)-7H-thieno[2,3-b]pyridine-4,6-dione
2-chloro-5-fluoro-3-(4-methoxyphenyl)-5-phenyl-7H-thieno[2,3-b]pyridine-4,6-dione
2-chloro-5-fluoro-5-(3-methylsulfonylphenyl)-3-phenyl-7H-thieno[2,3-b]pyridine-4,6-dione
2-chloro-3-(4-fluorophenyl)-5-methyl-5-(m-tolyl)-7H-thieno[2,3-b]pyridine-4,6-dione
2-chloro-3-(2-fluorophenyl)-5-(4-methoxyphenyl)-5-methyl-7H-thieno[2,3-b]pyridine-4,6-dione
2-chloro-5-(3-fluorophenyl)-3-(4-methoxyphenyl)-5-methyl-7H-thieno[2,3-b]pyridine-4,6-dione
2-chloro-3,5-bis(4-methoxyphenyl)-5-methyl-7H-thieno[2,3-b]pyridine-4,6-dione
2-chloro-3-(4-methoxyphenyl)-5-methyl-5-(m-tolyl)-7H-thieno[2,3-b]pyridine-4,6-dione
2-chloro-5-(3-methoxyphenyl)-3-(4-methoxyphenyl)-5-methyl-7H-thieno[2,3-b]pyridine-4,6-dione
2-chloro-3,5-bis(2-fluorophenyl)-5-methyl-7H-thieno[2,3-b]pyridine-4,6-dione
2-chloro-3-(2-fluorophenyl)-5-(3-fluorophenyl)-5-methyl-7H-thieno[2,3-b]pyridine-4,6-dione
2-chloro-3-(2-fluorophenyl)-5-(4-fluorophenyl)-5-methyl-7H-thieno[2,3-b]pyridine-4,6-dione
2-chloro-3-(2-fluorophenyl)-5-methyl-5-(m-tolyl)-7H-thieno[2,3-b]pyridine-4,6-dione
2-chloro-5-fluoro-5-phenyl-3-(4-pyridyl)-7H-thieno[2,3-b]pyridine-4,6-dione
2-chloro-5-fluoro-3-(3-methoxyphenyl)-5-phenyl-7H-thieno[2,3-b]pyridine-4,6-dione
2-chloro-5-fluoro-3-phenyl-5-[3-(trifluoromethyl)phenyl]-7H-thieno[2,3-b]pyridine-4,6-dione
2-chloro-3-(4-methoxyphenyl)-5-methyl-5-(p-tolyl)-7H-thieno[2,3-b]pyridine-4,6-dione
2-chloro-5-fluoro-5-(4-methylsulfonylphenyl)-3-phenyl-7H-thieno[2,3-b]pyridine-4,6-dione
2-chloro-5-fluoro-3-(2-methoxyphenyl)-5-phenyl-7H-thieno[2,3-b]pyridine-4,6-dione
2-chloro-5-fluoro-3-(4-fluoro-2-hydroxy-phenyl)-5-(2-methoxyphenyl)-7H-thieno[2,3-b]pyridine-4,6-dione
5-fluoro-3,5-diphenyl-7H-thieno[2,3-b]pyridine-4,6-dione
2-chloro-3-(2-chlorophenyl)-5-fluoro-5-phenyl-7H-thieno[2,3-b]pyridine-4,6-dione
5-fluoro-3-(4-fluoro-2-hydroxy-3-methyl-phenyl)-5-phenyl-7H-thieno[2,3-b]pyridine-4,6-dione
2-chloro-3,5-bis(3-fluorophenyl)-5-methyl-7H-thieno[2,3-b]pyridine-4,6-dione
2-chloro-5-(2-fluorophenyl)-3-(3-fluorophenyl)-5-methyl-7H-thieno[2,3-b]pyridine-4,6-dione
2-chloro-3-(3-fluorophenyl)-5-(3-methoxyphenyl)-5-methyl-7H-thieno[2,3-b]pyridine-4,6-dione
2-chloro-3-(3-fluorophenyl)-5-methyl-5-(m-tolyl)-7H-thieno[2,3-b]pyridine-4,6-dione
2-chloro-3-(2-methoxyphenyl)-5-methyl-5-phenyl-7H-thieno[2,3-b]pyridine-4,6-dione
5-fluoro-3-(4-fluoro-2-hydroxy-3-methyl-phenyl)-5-(4-fluorophenyl)-7H-thieno[2,3-b]pyridine-4,6-dione
5-fluoro-3-(4-fluoro-2-hydroxy-phenyl)-5-(p-tolyl)-7H-thieno[2,3-b]pyridine-4,6-dione
3-[5-fluoro-3-(2-methoxy-4-methyl-phenyl)-4,6-dioxo-7H-thieno[2,3-b]pyridin-5-yl]benzonitrile
3-[2,5-difluoro-3-(2-methoxy-4-methyl-phenyl)-4,6-dioxo-7H-thieno[2,3-b]pyridin-5-yl]benzonitrile
5-fluoro-3-(2-hydroxy-6-methoxy-phenyl)-5-phenyl-7H-thieno[2,3-b]pyridine-4,6-dione
5-fluoro-3-(3-methoxy-4-methyl-phenyl)-5-phenyl-7H-thieno[2,3-b]pyridine-4,6-dione
2,5-difluoro-3-(3-methoxy-4-methyl-phenyl)-5-phenyl-7H-thieno[2,3-b]pyridine-4,6-dione
5-fluoro-3-(3-hydroxy-4-methyl-phenyl)-5-phenyl-7H-thieno[2,3-b]pyridine-4,6-dione
2,5-difluoro-3-(3-hydroxy-4-methyl-phenyl)-5-phenyl-7H-thieno[2,3-b]pyridine-4,6-dione
2-chloro-5-methyl-3-(m-tolyl)-5-(p-tolyl)-7H-thieno[2,3-b]pyridine-4,6-dione
5-fluoro-3-(2-methoxy-4-methyl-phenyl)-5-phenyl-7H-thieno[2,3-b]pyridine-4,6-dione
2,5-difluoro-3-(2-methoxy-4-methyl-phenyl)-5-phenyl-7H-thieno[2,3-b]pyridine-4,6-dione
5-fluoro-3-(3-methylsulfonylphenyl)-5-phenyl-7H-thieno[2,3-b]pyridine-4,6-dione
5-fluoro-3-(2-hydroxy-4-methyl-phenyl)-5-phenyl-7H-thieno[2,3-b]pyridine-4,6-dione
3-(2,6-difluorophenyl)-5-fluoro-5-phenyl-7H-thieno[2,3-b]pyridine-4,6-dione
3-(4-bromo-2-hydroxy-phenyl)-5-fluoro-5-phenyl-7H-thieno[2,3-b]pyridine-4,6-dione
3-(4-bromophenyl)-5-fluoro-5-(4-pyridyl)-7H-thieno[2,3-b]pyridine-4,6-dione
3-(2-bromophenyl)-5-fluoro-5-phenyl-7H-thieno[2,3-b]pyridine-4,6-dione
2-chloro-5-(3-methoxyphenyl)-5-methyl-3-(m-tolyl)-7H-thieno[2,3-b]pyridine-4,6-dione
3-(4-bromo-2-methoxy-phenyl)-5-fluoro-5-phenyl-7H-thieno[2,3-b]pyridine-4,6-dione
3-(4-bromo-2-methoxy-phenyl)-2,5-difluoro-5-phenyl-7H-thieno[2,3-b]pyridine-4,6-dione
5-fluoro-3-(o-tolyl)-5-phenyl-7H-thieno[2,3-b]pyridine-4,6-dione
2,5-difluoro-3-(o-tolyl)-5-phenyl-7H-thieno[2,3-b]pyridine-4,6-dione
5-fluoro-3-phenyl-5-[3-(trifluoromethyl)phenyl]-7H-thieno[2,3-b]pyridine-4,6-dione
2,5-difluoro-3-phenyl-5-[3-(trifluoromethyl)phenyl]-7H-thieno[2,3-b]pyridine-4,6-dione
5-fluoro-3-phenyl-5-[4-(trifluoromethyl)phenyl]-7H-thieno[2,3-b]pyridine-4,6-dione
2,5-difluoro-3-phenyl-5-[4-(trifluoromethyl)phenyl]-7H-thieno[2,3-b]pyridine-4,6-dione 5-fluoro-5-phenyl-3-[4-(trifluoromethyl)phenyl]-7H-thieno[2,3-b]pyridine-4,6-dione
5-fluoro-3-(m-tolyl)-5-phenyl-7H-thieno[2,3-b]pyridine-4,6-dione
2,5-difluoro-3-(m-tolyl)-5-phenyl-7H-thieno[2,3-b]pyridine-4,6-dione
3-(2-chlorophenyl)-5-fluoro-5-phenyl-7H-thieno[2,3-b]pyridine-4,6-dione
2-chloro-3-(2-fluorophenyl)-5-methyl-5-(3-methylsulfonylphenyl)-7H-thieno[2,3-b]pyridine-4,6-dione
2-chloro-5-(4-hydroxyphenyl)-5-methyl-3-phenyl-7H-thieno[2,3-b]pyridine-4,6-dione
2-chloro-3-(2-methoxyphenyl)-5-methyl-5-(4-methylsulfonylphenyl)-7H-thieno[2,3-b]pyridine-4,6-dione
3-(4-tert-butylphenyl)-5-fluoro-5-phenyl-7H-thieno[2,3-b]pyridine-4,6-dione
3-(4-tert-butylphenyl)-2-chloro-5-fluoro-5-phenyl-7H-thieno[2,3-b]pyridine-4,6-dione
2-chloro-5-methyl-5-(m-tolyl)-3-(p-tolyl)-7H-thieno[2,3-b]pyridine-4,6-dione
2-chloro-3-(2-methoxyphenyl)-5-methyl-5-phenyl-7H-thieno[2,3-b]pyridine-4,6-dione
2-chloro-3-(3-fluorophenyl)-5-(4-methoxyphenyl)-5-methyl-7H-thieno[2,3-b]pyridine-4,6-dione
5-fluoro-3-(2-hydroxyphenyl)-5-phenyl-7H-thieno[2,3-b]pyridine-4,6-dione
2-chloro-3-(3-fluorophenyl)-5-methyl-5-(3-methylsulfonylphenyl)-7H-thieno[2,3-b]pyridine-4,6-dione
2-chloro-3-(3-fluorophenyl)-5-methyl-5-(4-methylsulfonylphenyl)-7H-thieno[2,3-b]pyridine-4,6-dione
2-chloro-5-(4-methoxyphenyl)-5-methyl-3-(p-tolyl)-7H-thieno[2,3-b]pyridine-4,6-dione
3-(2-benzyloxy-5-fluoro-phenyl)-2-chloro-5-fluoro-5-phenyl-7H-thieno[2,3-b]pyridine-4,6-dione
3-(2-benzyloxy-5-methoxy-phenyl)-5-fluoro-5-phenyl-7H-thieno[2,3-b]pyridine-4,6-dione
2-chloro-5-(2-fluorophenyl)-3-(4-methoxyphenyl)-5-methyl-7H-thieno[2,3-b]pyridine-4,6-dione
2-chloro-5-methyl-3,5-bis(p-tolyl)-7H-thieno[2,3-b]pyridine-4,6-dione
2-chloro-5-(4-methoxyphenyl)-5-methyl-3-(m-tolyl)-7H-thieno[2,3-b]pyridine-4,6-dione
2-chloro-5-(2-fluorophenyl)-5-methyl-3-(m-tolyl)-7H-thieno[2,3-b]pyridine-4,6-dione
2-chloro-5-fluoro-3-(3-fluorophenyl)-5-phenyl-7H-thieno[2,3-b]pyridine-4,6-dione
2-chloro-5-(3-fluorophenyl)-5-methyl-3-(m-tolyl)-7H-thieno[2,3-b]pyridine-4,6-dione
3-(4-bromo-3-methoxy-phenyl)-5-fluoro-5-phenyl-7H-thieno[2,3-b]pyridine-4,6-dione
3-(4-bromo-3-methoxy-phenyl)-2,5-difluoro-5-phenyl-7H-thieno[2,3-b]pyridine-4,6-dione
5-fluoro-3-(2-naphthyl)-5-phenyl-7H-thieno[2,3-b]pyridine-4,6-dione
2,5-difluoro-3-(2-naphthyl)-5-phenyl-7H-thieno[2,3-b]pyridine-4,6-dione
3-(3-bromophenyl)-5-fluoro-5-phenyl-7H-thieno[2,3-b]pyridine-4,6-dione
3-(3-bromophenyl)-2,5-difluoro-5-phenyl-7H-thieno[2,3-b]pyridine-4,6-dione
2,5-difluoro-3-(4-fluorophenyl)-5-(4-methoxyphenyl)-7H-thieno[2,3-b]pyridine-4,6-dione
3-(4-bromophenyl)-5-fluoro-5-(3-pyridyl)-7H-thieno[2,3-b]pyridine-4,6-dione
5-fluoro-5-(4-methoxyphenyl)-3-phenyl-7H-thieno[2,3-b]pyridine-4,6-dione
2,5-difluoro-5-(4-methoxyphenyl)-3-phenyl-7H-thieno[2,3-b]pyridine-4,6-dione
2-chloro-5-fluoro-3-(4-fluoro-2-hydroxy-phenyl)-5-(4-methoxyphenyl)-7H-thieno[2,3-b]pyridine-4,6-dione
2-chloro-5-(4-fluorophenyl)-5-methyl-3-(m-tolyl)-7H-thieno[2,3-b]pyridine-4,6-dione
2-chloro-5-methyl-3,5-bis(m-tolyl)-7H-thieno[2,3-b]pyridine-4,6-dione
3-(4-chlorophenyl)-5-fluoro-5-phenyl-7H-thieno[2,3-b]pyridine-4,6-dione
3-(4-chlorophenyl)-2,5-difluoro-5-phenyl-7H-thieno[2,3-b]pyridine-4,6-dione
3-(2-benzyloxy-4-fluoro-phenyl)-5-fluoro-5-phenyl-7H-thieno[2,3-b]pyridine-4,6-dione
3-(2-benzyloxy-4-fluoro-phenyl)-2,5-difluoro-5-phenyl-7H-thieno[2,3-b]pyridine-4,6-dione
2,5-dichloro-3-(4-fluoro-2-hydroxy-phenyl)-5-(m-tolyl)-7H-thieno[2,3-b]pyridine-4,6-dione
5-fluoro-3-(2-fluorophenyl)-5-phenyl-7H-thieno[2,3-b]pyridine-4,6-dione
2,5-difluoro-3-(2-fluorophenyl)-5-phenyl-7H-thieno[2,3-b]pyridine-4,6-dione
3-(2,4-difluorophenyl)-5-fluoro-5-phenyl-7H-thieno[2,3-b]pyridine-4,6-dione
5-fluoro-3-(2-methoxyphenyl)-5-phenyl-7H-thieno[2,3-b]pyridine-4,6-dione
2,5-difluoro-3-(2-methoxyphenyl)-5-phenyl-7H-thieno[2,3-b]pyridine-4,6-dione
5-fluoro-5-(3-methoxyphenyl)-3-phenyl-7H-thieno[2,3-b]pyridine-4,6-dione
2,5-difluoro-5-(3-methoxyphenyl)-3-phenyl-7H-thieno[2,3-b]pyridine-4,6-dione
2-chloro-5-fluoro-3-(4-fluoro-2-hydroxy-phenyl)-5-(m-tolyl)-7H-thieno[2,3-b]pyridine-4,6-dione
2-chloro-5-fluoro-3-(4-fluoro-2-hydroxy-3-methyl-phenyl)-5-phenyl-7H-thieno[2,3-b]pyridine-4,6-dione
2-chloro-3-(3,4-dimethylphenyl)-5-fluoro-5-(m-tolyl)-7H-thieno[2,3-b]pyridine-4,6-dione
2-chloro-3-(3,4-dimethylphenyl)-5-fluoro-5-(3-pyridyl)-7H-thieno[2,3-b]pyridine-4,6-dione
3-(4-bromophenyl)-5-fluoro-5-(2-pyridyl)-7H-thieno[2,3-b]pyridine-4,6-dione
5-fluoro-3-(4-fluorophenyl)-5-phenyl-7H-thieno[2,3-b]pyridine-4,6-dione
5-fluoro-3-(3-fluorophenyl)-5-phenyl-7H-thieno[2,3-b]pyridine-4,6-dione
2-chloro-5-fluoro-3-(3-fluoro-2-hydroxy-4-methyl-phenyl)-5-phenyl-7H-thieno[2,3-b]pyridine-4,6-dione
5-fluoro-3-(3-fluoro-2-hydroxy-4-methyl-phenyl)-2-methyl-5-phenyl-7H-thieno[2,3-b]pyridine-4,6-dione
5-fluoro-5-phenyl-3-pyrazin-2-yl-7H-thieno[2,3-b]pyridine-4,6-dione
5-fluoro-3-(3-fluoro-4-hydroxy-phenyl)-5-phenyl-7H-thieno[2,3-b]pyridine-4,6-dione
2,5-difluoro-3-(3-fluoro-4-methoxy-phenyl)-5-phenyl-7H-thieno[2,3-b]pyridine-4,6-dione
3-(5-fluoro-4,6-dioxo-5-phenyl-7H-thieno[2,3-b]pyridin-3-yl)benzoic acid
3-(2,5-difluoro-4,6-dioxo-5-phenyl-7H-thieno[2,3-b]pyridin-3-yl)benzoic acid
4-(5-fluoro-4,6-dioxo-5-phenyl-7H-thieno[2,3-b]pyridin-3-yl)benzoic acid
5-fluoro-5-(4-fluorophenyl)-3-(4-methoxyphenyl)-7H-thieno[2,3-b]pyridine-4,6-dione
2,5-difluoro-5-(4-fluorophenyl)-3-(4-methoxyphenyl)-7H-thieno[2,3-b]pyridine-4,6-dione 5-fluoro-3-(4-methoxyphenyl)-5-phenyl-7H-thieno[2,3-b]pyridine-4,6-dione
2,5-difluoro-3-(4-methoxyphenyl)-5-phenyl-7H-thieno[2,3-b]pyridine-4,6-dione
5-fluoro-3-(4-hydroxyphenyl)-5-phenyl-7H-thieno[2,3-b]pyridine-4,6-dione
5-fluoro-3-(3-hydroxyphenyl)-5-phenyl-7H-thieno[2,3-b]pyridine-4,6-dione
5-fluoro-3-(3-methoxyphenyl)-5-phenyl-7H-thieno[2,3-b]pyridine-4,6-dione
2,5-difluoro-3-(3-methoxyphenyl)-5-phenyl-7H-thieno[2,3-b]pyridine-4,6-dione
5-fluoro-5-(2-methoxyphenyl)-3-phenyl-7H-thieno[2,3-b]pyridine-4,6-dione
5-fluoro-5-phenyl-3-(4-pyridyl)-7H-thieno[2,3-b]pyridine-4,6-dione
2-chloro-5-(3-methoxyphenyl)-5-methyl-3-(p-tolyl)-7H-thieno[2,3-b]pyridine-4,6-dione
2-chloro-5-fluoro-3-(3-fluorophenyl)-5-(m-tolyl)-7H-thieno[2,3-b]pyridine-4,6-dione
3-[2-chloro-5-fluoro-3-(3-fluorophenyl)-4,6-dioxo-7H-thieno[2,3-b]pyridin-5-yl]benzonitrile
2-chloro-5-fluoro-3-(3-fluorophenyl)-5-(3-pyridyl)-7H-thieno[2,3-b]pyridine-4,6-dione
2-chloro-5-fluoro-3-(2-hydroxy-3-methyl-phenyl)-5-phenyl-7H-thieno[2,3-b]pyridine-4,6-dione
5-fluoro-5-phenyl-3-(3-pyridyl)-7H-thieno[2,3-b]pyridine-4,6-dione
2-chloro-5-fluoro-3-(4-fluoro-2-hydroxy-phenyl)-5-(3-fluorophenyl)-7H-thieno[2,3-b]pyridine-4,6-dione
2,5-dichloro-3-(4-fluoro-2-hydroxy-phenyl)-5-phenyl-7H-thieno[2,3-b]pyridine-4,6-dione
3-[2-chloro-3-(3,4-dimethylphenyl)-5-fluoro-4,6-dioxo-7H-thieno[2,3-b]pyridin-5-yl]benzonitrile
2-chloro-5-fluoro-3-(4-fluoro-2-hydroxy-phenyl)-5-(4-methylsulfonylphenyl)-7H-thieno[2,3-b]pyridine-4,6-dione
2-chloro-5-(3,4-dimethoxyphenyl)-5-fluoro-3-(4-fluoro-2-hydroxy-phenyl)-7H-thieno[2,3-b]pyridine-4,6-dione
5-fluoro-3-(4-fluoro-2-hydroxy-phenyl)-2-methyl-5-phenyl-7H-thieno[2,3-b]pyridine-4,6-dione
2-chloro-5-fluoro-3-(5-fluoro-2-hydroxy-phenyl)-5-phenyl-7H-thieno[2,3-b]pyridine-4,6-dione
2,5-dichloro-3,5-diphenyl-7H-thieno[2,3-b]pyridine-4,6-dione
2-chloro-3-(4-ethyl-2-hydroxy-phenyl)-5-fluoro-5-phenyl-7H-thieno[2,3-b]pyridine-4,6-dione
3-[2-chloro-5-fluoro-3-(4-fluoro-2-hydroxy-phenyl)-4,6-dioxo-7H-thieno[2,3-b]pyridin-5-yl]benzonitrile
2-chloro-5-fluoro-3-(4-fluoro-2-hydroxy-phenyl)-5-(4-methoxy-3-methyl-phenyl)-7H-thieno[2,3-b]pyridine-4,6-dione
2-chloro-5-fluoro-3-(4-fluoro-2-hydroxy-phenyl)-5-(3-thienyl)-7H-thieno[2,3-b]pyridine-4,6-dione
2-chloro-5-fluoro-3-(3-fluoro-2-methoxy-4-methyl-phenyl)-5-(4-fluorophenyl)-7H-thieno[2,3-b]pyridine-4,6-dione
2-chloro-5-fluoro-3-(3-fluoro-2-hydroxy-4-methyl-phenyl)-5-(4-fluorophenyl)-7H-thieno[2,3-b]pyridine-4,6-dione
2-chloro-5-fluoro-3-(4-fluoro-2-methoxy-3-methyl-phenyl)-5-phenyl-7H-thieno[2,3-b]pyridine-4,6-dione
2-chloro-5-fluoro-3-(3-fluoro-2-methoxy-4-methyl-phenyl)-5-phenyl-7H-thieno[2,3-b]pyridine-4,6-dione
2-chloro-3-(4-fluoro-2-hydroxy-phenyl)-5-methoxy-5-phenyl-7H-thieno[2,3-b]pyridine-4,6-dione
2,5-dichloro-3-(3-fluoro-2-hydroxy-4-methyl-phenyl)-5-phenyl-7H-thieno[2,3-b]pyridine-4,6-dione
2,5-dichloro-3-(4-fluoro-2-hydroxy-3-methyl-phenyl)-5-phenyl-7H-thieno[2,3-b]pyridine-4,6-dione In a preferred embodiment, compounds of formula (1) are the following:
2-chloro-5-methyl-3,5-diphenyl-7H-thieno[2,3-b]pyridine-4,6-dione
2-chloro-3-(2-fluoro-4-methoxy-phenyl)-5-methyl-5-phenyl-7H-thieno[2,3-b]pyridine-4,6-dione
2-chloro-5-fluoro-3,5-diphenyl-7H-thieno[2,3-b]pyridine-4,6-dione
2-chloro-5-(4-ethoxyphenyl)-3-(2-fluoro-4-methyl-phenyl)-5-methyl-7H-thieno[2,3-b]pyridine-4,6-dione
5-fluoro-3-(4-fluoro-2-hydroxy-phenyl)-5-phenyl-7H-thieno[2,3-b]pyridine-4,6-dione
2-chloro-3-(3-fluorophenyl)-5-methyl-5-phenyl-7H-thieno[2,3-b]pyridine-4,6-dione
2-chloro-5-fluoro-3-(4-fluoro-2-hydroxy-phenyl)-5-phenyl-7H-thieno[2,3-b]pyridine-4,6-dione
2-chloro-5-(2-fluorophenyl)-3-(4-fluorophenyl)-5-methyl-7H-thieno[2,3-b]pyridine-4,6-dione
2-chloro-5-(4-fluorophenyl)-5-methyl-3-(p-tolyl)-7H-thieno[2,3-b]pyridine-4,6-dione
2-chloro-5-(3-methoxyphenyl)-5-methyl-3-(o-tolyl)-7H-thieno[2,3-b]pyridine-4,6-dione
2-chloro-5-methyl-5-(m-tolyl)-3-(o-tolyl)-7H-thieno[2,3-b]pyridine-4,6-dione
2-chloro-3-(3-fluorophenyl)-5-methyl-5-(p-tolyl)-7H-thieno[2,3-b]pyridine-4,6-dione
2-chloro-3,5-bis(3-methoxyphenyl)-5-methyl-7H-thieno[2,3-b]pyridine-4,6-dione
2-chloro-5-(3-fluorophenyl)-3-(3-methoxyphenyl)-5-methyl-7H-thieno[2,3-b]pyridine-4,6-dione
2-chloro-3-(4-fluorophenyl)-5-(3-methoxyphenyl)-5-methyl-7H-thieno[2,3-b]pyridine-4,6-dione
2-chloro-3-(4-fluorophenyl)-5-methyl-5-(3-methylsulfonylphenyl)-7H-thieno[2,3-b]pyridine-4,6-dione
2-chloro-3-(2-methoxyphenyl)-5-methyl-5-(p-tolyl)-7H-thieno[2,3-b]pyridine-4,6-dione
2-chloro-5-(3-fluorophenyl)-3-(2-methoxyphenyl)-5-methyl-7H-thieno[2,3-b]pyridine-4,6-dione
2-chloro-3-(2-methoxyphenyl)-5-(4-methoxyphenyl)-5-methyl-7H-thieno[2,3-b]pyridine-4,6-dione
2-chloro-3-(2-methoxyphenyl)-5-(3-methoxyphenyl)-5-methyl-7H-thieno[2,3-b]pyridine-4,6-dione
2-chloro-5-(2-fluorophenyl)-3-(2-methoxyphenyl)-5-methyl-7H-thieno[2,3-b]pyridine-4,6-dione
5-fluoro-2-methyl-3,5-diphenyl-7H-thieno[2,3-b]pyridine-4,6-dione
2-chloro-5-fluoro-5-phenyl-3-(3-pyridyl)-7H-thieno[2,3-b]pyridine-4,6-dione
2-chloro-5-fluoro-3-(4-hydroxyphenyl)-5-phenyl-7H-thieno[2,3-b]pyridine-4,6-dione
2-chloro-5-fluoro-3-(2-fluorophenyl)-5-phenyl-7H-thieno[2,3-b]pyridine-4,6-dione
2-chloro-5-fluoro-3-(2-fluoro-4-methoxy-phenyl)-5-phenyl-7H-thieno[2,3-b]pyridine-4,6-dione
2-chloro-5-fluoro-3-(3-fluoro-4-hydroxy-phenyl)-5-phenyl-7H-thieno[2,3-b]pyridine-4,6-dione
2-chloro-5-fluoro-3-(m-tolyl)-5-phenyl-7H-thieno[2,3-b]pyridine-4,6-dione
2-chloro-5-fluoro-5-phenyl-3-(p-tolyl)-7H-thieno[2,3-b]pyridine-4,6-dione
2-chloro-5-fluoro-3-(4-methoxyphenyl)-5-phenyl-7H-thieno[2,3-b]pyridine-4,6-dione
2-chloro-3-(2-fluorophenyl)-5-(4-methoxyphenyl)-5-methyl-7H-thieno[2,3-b]pyridine-4,6-dione 2-chloro-5-fluoro-3-(3-methoxyphenyl)-5-phenyl-7H-thieno[2,3-b]pyridine-4,6-dione
2-chloro-5-fluoro-3-phenyl-5-[3-(trifluoromethyl)phenyl]-7H-thieno[2,3-b]pyridine-4,6-dione
2-chloro-5-fluoro-5-(4-methylsulfonylphenyl)-3-phenyl-7H-thieno[2,3-b]pyridine-4,6-dione
2-chloro-5-fluoro-3-(4-fluoro-2-hydroxy-phenyl)-5-(2-methoxyphenyl)-7H-thieno[2,3-b]pyridine-4,6-dione
5-fluoro-3,5-diphenyl-7H-thieno[2,3-b]pyridine-4,6-dione
2-chloro-3-(2-chlorophenyl)-5-fluoro-5-phenyl-7H-thieno[2,3-b]pyridine-4,6-dione
5-fluoro-3-(4-fluoro-2-hydroxy-3-methyl-phenyl)-5-phenyl-7H-thieno[2,3-b]pyridine-4,6-dione
2-chloro-5-(2-fluorophenyl)-3-(3-fluorophenyl)-5-methyl-7H-thieno[2,3-b]pyridine-4,6-dione
5-fluoro-3-(4-fluoro-2-hydroxy-3-methyl-phenyl)-5-(4-fluorophenyl)-7H-thieno[2,3-b]pyridine-4,6-dione
5-fluoro-3-(4-fluoro-2-hydroxy-phenyl)-5-(p-tolyl)-7H-thieno[2,3-b]pyridine-4,6-dione
3-[5-fluoro-3-(2-methoxy-4-methyl-phenyl)-4,6-dioxo-7H-thieno[2,3-b]pyridin-5-yl]benzonitrile
3-[2,5-difluoro-3-(2-methoxy-4-methyl-phenyl)-4,6-dioxo-7H-thieno[2,3-b]pyridin-5-yl]benzonitrile
5-fluoro-3-(3-methoxy-4-methyl-phenyl)-5-phenyl-7H-thieno[2,3-b]pyridine-4,6-dione
2,5-difluoro-3-(3-methoxy-4-methyl-phenyl)-5-phenyl-7H-thieno[2,3-b]pyridine-4,6-dione
5-fluoro-3-(3-hydroxy-4-methyl-phenyl)-5-phenyl-7H-thieno[2,3-b]pyridine-4,6-dione
2,5-difluoro-3-(3-hydroxy-4-methyl-phenyl)-5-phenyl-7H-thieno[2,3-b]pyridine-4,6-dione
5-fluoro-3-(2-methoxy-4-methyl-phenyl)-5-phenyl-7H-thieno[2,3-b]pyridine-4,6-dione
2,5-difluoro-3-(2-methoxy-4-methyl-phenyl)-5-phenyl-7H-thieno[2,3-b]pyridine-4,6-dione
5-fluoro-3-(2-hydroxy-4-methyl-phenyl)-5-phenyl-7H-thieno[2,3-b]pyridine-4,6-dione
3-(2,6-difluorophenyl)-5-fluoro-5-phenyl-7H-thieno[2,3-b]pyridine-4,6-dione
3-(4-bromo-2-hydroxy-phenyl)-5-fluoro-5-phenyl-7H-thieno[2,3-b]pyridine-4,6-dione
3-(4-bromophenyl)-5-fluoro-5-(4-pyridyl)-7H-thieno[2,3-b]pyridine-4,6-dione
2-chloro-5-(3-methoxyphenyl)-5-methyl-3-(m-tolyl)-7H-thieno[2,3-b]pyridine-4,6-dione
5-fluoro-3-(o-tolyl)-5-phenyl-7H-thieno[2,3-b]pyridine-4,6-dione
2,5-difluoro-3-(o-tolyl)-5-phenyl-7H-thieno[2,3-b]pyridine-4,6-dione
5-fluoro-3-phenyl-5-[3-(trifluoromethyl)phenyl]-7H-thieno[2,3-b]pyridine-4,6-dione
5-fluoro-3-(m-tolyl)-5-phenyl-7H-thieno[2,3-b]pyridine-4,6-dione
2,5-difluoro-3-(m-tolyl)-5-phenyl-7H-thieno[2,3-b]pyridine-4,6-dione
3-(2-chlorophenyl)-5-fluoro-5-phenyl-7H-thieno[2,3-b]pyridine-4,6-dione
5-fluoro-3-(2-hydroxyphenyl)-5-phenyl-7H-thieno[2,3-b]pyridine-4,6-dione
3-(2-benzyloxy-5-methoxy-phenyl)-5-fluoro-5-phenyl-7H-thieno[2,3-b]pyridine-4,6-dione
2-chloro-5-fluoro-3-(3-fluorophenyl)-5-phenyl-7H-thieno[2,3-b]pyridine-4,6-dione
3-(4-bromo-3-methoxy-phenyl)-5-fluoro-5-phenyl-7H-thieno[2,3-b]pyridine-4,6-dione
3-(4-bromo-3-methoxy-phenyl)-2,5-difluoro-5-phenyl-7H-thieno[2,3-b]pyridine-4,6-dione
5-fluoro-3-(2-naphthyl)-5-phenyl-7H-thieno[2,3-b]pyridine-4,6-dione
2,5-difluoro-3-(2-naphthyl)-5-phenyl-7H-thieno[2,3-b]pyridine-4,6-dione
3-(3-bromophenyl)-5-fluoro-5-phenyl-7H-thieno[2,3-b]pyridine-4,6-dione
3-(3-bromophenyl)-2,5-difluoro-5-phenyl-7H-thieno[2,3-b]pyridine-4,6-dione
2,5-difluoro-3-(4-fluorophenyl)-5-(4-methoxyphenyl)-7H-thieno[2,3-b]pyridine-4,6-dione
2-chloro-5-fluoro-3-(4-fluoro-2-hydroxy-phenyl)-5-(4-methoxyphenyl)-7H-thieno[2,3-b]pyridine-4,6-dione
3-(4-chlorophenyl)-5-fluoro-5-phenyl-7H-thieno[2,3-b]pyridine-4,6-dione
3-(4-chlorophenyl)-2,5-difluoro-5-phenyl-7H-thieno[2,3-b]pyridine-4,6-dione
2,5-dichloro-3-(4-fluoro-2-hydroxy-phenyl)-5-(m-tolyl)-7H-thieno[2,3-b]pyridine-4,6-dione
2,5-difluoro-3-(2-fluorophenyl)-5-phenyl-7H-thieno[2,3-b]pyridine-4,6-dione
5-fluoro-5-(3-methoxyphenyl)-3-phenyl-7H-thieno[2,3-b]pyridine-4,6-dione
2,5-difluoro-5-(3-methoxyphenyl)-3-phenyl-7H-thieno[2,3-b]pyridine-4,6-dione
2-chloro-5-fluoro-3-(4-fluoro-2-hydroxy-phenyl)-5-(m-tolyl)-7H-thieno[2,3-b]pyridine-4,6-dione
2-chloro-5-fluoro-3-(4-fluoro-2-hydroxy-3-methyl-phenyl)-5-phenyl-7H-thieno[2,3-b]pyridine-4,6-dione
2-chloro-3-(3,4-dimethylphenyl)-5-fluoro-5-(m-tolyl)-7H-thieno[2,3-b]pyridine-4,6-dione
2-chloro-3-(3,4-dimethylphenyl)-5-fluoro-5-(3-pyridyl)-7H-thieno[2,3-b]pyridine-4,6-dione
5-fluoro-3-(3-fluorophenyl)-5-phenyl-7H-thieno[2,3-b]pyridine-4,6-dione
2-chloro-5-fluoro-3-(3-fluoro-2-hydroxy-4-methyl-phenyl)-5-phenyl-7H-thieno[2,3-b]pyridine-4,6-dione
5-fluoro-3-(3-fluoro-2-hydroxy-4-methyl-phenyl)-2-methyl-5-phenyl-7H-thieno[2,3-b]pyridine-4,6-dione
5-fluoro-3-(3-fluoro-4-hydroxy-phenyl)-5-phenyl-7H-thieno[2,3-b]pyridine-4,6-dione
2,5-difluoro-3-(3-fluoro-4-methoxy-phenyl)-5-phenyl-7H-thieno[2,3-b]pyridine-4,6-dione
5-fluoro-5-(4-fluorophenyl)-3-(4-methoxyphenyl)-7H-thieno[2,3-b]pyridine-4,6-dione
2,5-difluoro-5-(4-fluorophenyl)-3-(4-methoxyphenyl)-7H-thieno[2,3-b]pyridine-4,6-dione
5-fluoro-3-(4-methoxyphenyl)-5-phenyl-7H-thieno[2,3-b]pyridine-4,6-dione
2,5-difluoro-3-(4-methoxyphenyl)-5-phenyl-7H-thieno[2,3-b]pyridine-4,6-dione
5-fluoro-3-(4-hydroxyphenyl)-5-phenyl-7H-thieno[2,3-b]pyridine-4,6-dione
5-fluoro-3-(3-hydroxyphenyl)-5-phenyl-7H-thieno[2,3-b]pyridine-4,6-dione
5-fluoro-3-(3-methoxyphenyl)-5-phenyl-7H-thieno[2,3-b]pyridine-4,6-dione
2,5-difluoro-3-(3-methoxyphenyl)-5-phenyl-7H-thieno[2,3-b]pyridine-4,6-dione
2-chloro-5-fluoro-3-(3-fluorophenyl)-5-(m-tolyl)-7H-thieno[2,3-b]pyridine-4,6-dione
3-[2-chloro-5-fluoro-3-(3-fluorophenyl)-4,6-dioxo-7H-thieno[2,3-b]pyridin-5-yl]benzonitrile
2-chloro-5-fluoro-3-(3-fluorophenyl)-5-(3-pyridyl)-7H-thieno[2,3-b]pyridine-4,6-dione
2-chloro-5-fluoro-3-(2-hydroxy-3-methyl-phenyl)-5-phenyl-7H-thieno[2,3-b]pyridine-4,6-dione 2-chloro-5-fluoro-3-(4-fluoro-2-hydroxy-phenyl)-5-(3-fluorophenyl)-7H-thieno[2,3-b]pyridine-4,6-dione
2,5-dichloro-3-(4-fluoro-2-hydroxy-phenyl)-5-phenyl-7H-thieno[2,3-b]pyridine-4,6-dione
3-[2-chloro-3-(3,4-dimethylphenyl)-5-fluoro-4,6-dioxo-7H-thieno[2,3-b]pyridin-5-yl]benzonitrile
2-chloro-5-fluoro-3-(4-fluoro-2-hydroxy-phenyl)-5-(4-methylsulfonylphenyl)-7H-thieno[2,3-b]pyridine-4,6-dione
2-chloro-5-(3,4-dimethoxyphenyl)-5-fluoro-3-(4-fluoro-2-hydroxy-phenyl)-7H-thieno[2,3-b]pyridine-4,6-dione
5-fluoro-3-(4-fluoro-2-hydroxy-phenyl)-2-methyl-5-phenyl-7H-thieno[2,3-b]pyridine-4,6-dione
2-chloro-5-fluoro-3-(5-fluoro-2-hydroxy-phenyl)-5-phenyl-7H-thieno[2,3-b]pyridine-4,6-dione
2,5-dichloro-3,5-diphenyl-7H-thieno[2,3-b]pyridine-4,6-dione
2-chloro-3-(4-ethyl-2-hydroxy-phenyl)-5-fluoro-5-phenyl-7H-thieno[2,3-b]pyridine-4,6-dione
3-[2-chloro-5-fluoro-3-(4-fluoro-2-hydroxy-phenyl)-4,6-dioxo-7H-thieno[2,3-b]pyridin-5-yl]benzonitrile
2-chloro-5-fluoro-3-(4-fluoro-2-hydroxy-phenyl)-5-(4-methoxy-3-methyl-phenyl)-7H-thieno[2,3-b]pyridine-4,6-dione
2-chloro-5-fluoro-3-(4-fluoro-2-hydroxy-phenyl)-5-(3-thienyl)-7H-thieno[2,3-b]pyridine-4,6-dione
2-chloro-5-fluoro-3-(3-fluoro-2-methoxy-4-methyl-phenyl)-5-(4-fluorophenyl)-7H-thieno[2,3-b]pyridine-4,6-dione
2-chloro-5-fluoro-3-(3-fluoro-2-hydroxy-4-methyl-phenyl)-5-(4-fluorophenyl)-7H-thieno[2,3-b]pyridine-4,6-dione
2-chloro-3-(4-fluoro-2-hydroxy-phenyl)-5-methoxy-5-phenyl-7H-thieno[2,3-b]pyridine-4,6-dione
2,5-dichloro-3-(3-fluoro-2-hydroxy-4-methyl-phenyl)-5-phenyl-7H-thieno[2,3-b]pyridine-4,6-dione
2,5-dichloro-3-(4-fluoro-2-hydroxy-3-methyl-phenyl)-5-phenyl-7H-thieno[2,3-b]pyridine-4,6-dione.

In a further preferred embodiment, compounds of formula (1) are the following:
2-chloro-3-(2-fluoro-4-methoxy-phenyl)-5-methyl-5-phenyl-7H-thieno[2,3-b]pyridine-4,6-dione
2-chloro-5-fluoro-3,5-diphenyl-7H-thieno[2,3-b]pyridine-4,6-dione
5-fluoro-3-(4-fluoro-2-hydroxy-phenyl)-5-phenyl-7H-thieno[2,3-b]pyridine-4,6-dione
2-chloro-3-(3-fluorophenyl)-5-methyl-5-phenyl-7H-thieno[2,3-b]pyridine-4,6-dione
2-chloro-5-(3-methoxyphenyl)-5-methyl-3-(o-tolyl)-7H-thieno[2,3-b]pyridine-4,6-dione
2-chloro-5-methyl-5-(m-tolyl)-3-(o-tolyl)-7H-thieno[2,3-b]pyridine-4,6-dione
2-chloro-3-(3-fluorophenyl)-5-methyl-5-(p-tolyl)-7H-thieno[2,3-b]pyridine-4,6-dione
2-chloro-3,5-bis(3-methoxyphenyl)-5-methyl-7H-thieno[2,3-b]pyridine-4,6-dione
2-chloro-5-(3-fluorophenyl)-3-(3-methoxyphenyl)-5-methyl-7H-thieno[2,3-b]pyridine-4,6-dione
2-chloro-3-(4-fluorophenyl)-5-(3-methoxyphenyl)-5-methyl-7H-thieno[2,3-b]pyridine-4,6-dione
2-chloro-3-(4-fluorophenyl)-5-methyl-5-(3-methylsulfonylphenyl)-7H-thieno[2,3-b]pyridine-4,6-dione
2-chloro-3-(2-methoxyphenyl)-5-methyl-5-(p-tolyl)-7H-thieno[2,3-b]pyridine-4,6-dione
2-chloro-5-(3-fluorophenyl)-3-(2-methoxyphenyl)-5-methyl-7H-thieno[2,3-b]pyridine-4,6-dione
2-chloro-3-(2-methoxyphenyl)-5-(4-methoxyphenyl)-5-methyl-7H-thieno[2,3-b]pyridine-4,6-dione
2-chloro-3-(2-methoxyphenyl)-5-(3-methoxyphenyl)-5-methyl-7H-thieno[2,3-b]pyridine-4,6-dione
2-chloro-5-(2-fluorophenyl)-3-(2-methoxyphenyl)-5-methyl-7H-thieno[2,3-b]pyridine-4,6-dione
5-fluoro-2-methyl-3,5-diphenyl-7H-thieno[2,3-b]pyridine-4,6-dione
2-chloro-5-fluoro-3-(4-hydroxyphenyl)-5-phenyl-7H-thieno[2,3-b]pyridine-4,6-dione
2-chloro-5-fluoro-3-(2-fluorophenyl)-5-phenyl-7H-thieno[2,3-b]pyridine-4,6-dione
2-chloro-5-fluoro-3-(2-fluoro-4-methoxy-phenyl)-5-phenyl-7H-thieno[2,3-b]pyridine-4,6-dione
2-chloro-5-fluoro-3-(m-tolyl)-5-phenyl-7H-thieno[2,3-b]pyridine-4,6-dione
2-chloro-5-fluoro-5-phenyl-3-(p-tolyl)-7H-thieno[2,3-b]pyridine-4,6-dione
2-chloro-5-fluoro-3-(3-methoxyphenyl)-5-phenyl-7H-thieno[2,3-b]pyridine-4,6-dione
2-chloro-5-fluoro-5-(4-methylsulfonylphenyl)-3-phenyl-7H-thieno[2,3-b]pyridine-4,6-dione
2-chloro-5-fluoro-3-(4-fluoro-2-hydroxy-phenyl)-5-(2-methoxyphenyl)-7H-thieno[2,3-b]pyridine-4,6-dione
5-fluoro-3-(4-fluoro-2-hydroxy-3-methyl-phenyl)-5-phenyl-7H-thieno[2,3-b]pyridine-4,6-dione
2-chloro-5-(2-fluorophenyl)-3-(3-fluorophenyl)-5-methyl-7H-thieno[2,3-b]pyridine-4,6-dione
5-fluoro-3-(4-fluoro-2-hydroxy-3-methyl-phenyl)-5-(4-fluorophenyl)-7H-thieno[2,3-b]pyridine-4,6-dione
2,5-difluoro-3-(3-hydroxy-4-methyl-phenyl)-5-phenyl-7H-thieno[2,3-b]pyridine-4,6-dione
5-fluoro-3-(2-methoxy-4-methyl-phenyl)-5-phenyl-7H-thieno[2,3-b]pyridine-4,6-dione
2,5-difluoro-3-(2-methoxy-4-methyl-phenyl)-5-phenyl-7H-thieno[2,3-b]pyridine-4,6-dione
5-fluoro-3-(2-hydroxy-4-methyl-phenyl)-5-phenyl-7H-thieno[2,3-b]pyridine-4,6-dione
3-(2,6-difluorophenyl)-5-fluoro-5-phenyl-7H-thieno[2,3-b]pyridine-4,6-dione
3-(4-bromo-2-hydroxy-phenyl)-5-fluoro-5-phenyl-7H-thieno[2,3-b]pyridine-4,6-dione
2,5-difluoro-3-(m-tolyl)-5-phenyl-7H-thieno[2,3-b]pyridine-4,6-dione
5-fluoro-3-(2-hydroxyphenyl)-5-phenyl-7H-thieno[2,3-b]pyridine-4,6-dione
2-chloro-5-fluoro-3-(3-fluorophenyl)-5-phenyl-7H-thieno[2,3-b]pyridine-4,6-dione
3-(4-bromo-3-methoxy-phenyl)-5-fluoro-5-phenyl-7H-thieno[2,3-b]pyridine-4,6-dione
5-fluoro-3-(2-naphthyl)-5-phenyl-7H-thieno[2,3-b]pyridine-4,6-dione
2,5-difluoro-3-(2-naphthyl)-5-phenyl-7H-thieno[2,3-b]pyridine-4,6-dione
3-(3-bromophenyl)-2,5-difluoro-5-phenyl-7H-thieno[2,3-b]pyridine-4,6-dione
2,5-difluoro-3-(4-fluorophenyl)-5-(4-methoxyphenyl)-7H-thieno[2,3-b]pyridine-4,6-dione
2-chloro-5-fluoro-3-(4-fluoro-2-hydroxy-phenyl)-5-(4-methoxyphenyl)-7H-thieno[2,3-b]pyridine-4,6-dione
2,5-dichloro-3-(4-fluoro-2-hydroxy-phenyl)-5-(m-tolyl)-7H-thieno[2,3-b]pyridine-4,6-dione
5-fluoro-5-(3-methoxyphenyl)-3-phenyl-7H-thieno[2,3-b]pyridine-4,6-dione
2-chloro-5-fluoro-3-(4-fluoro-2-hydroxy-phenyl)-5-(m-tolyl)-7H-thieno[2,3-b]pyridine-4,6-dione
2-chloro-5-fluoro-3-(4-fluoro-2-hydroxy-3-methyl-phenyl)-5-phenyl-7H-thieno[2,3-b]pyridine-4,6-dione 2-chloro-3-(3,4-dimethylphenyl)-5-fluoro-5-(m-tolyl)-7H-thieno[2,3-b]pyridine-4,6-dione
2-chloro-3-(3,4-dimethylphenyl)-5-fluoro-5-(3-pyridyl)-7H-thieno[2,3-b]pyridine-4,6-dione
2-chloro-5-fluoro-3-(3-fluoro-2-hydroxy-4-methyl-phenyl)-5-phenyl-7H-thieno[2,3-b]pyridine-4,6-dione
5-fluoro-3-(3-fluoro-2-hydroxy-4-methyl-phenyl)-2-methyl-5-phenyl-7H-thieno[2,3-b]pyridine-4,6-dione
5-fluoro-3-(3-fluoro-4-hydroxy-phenyl)-5-phenyl-7H-thieno[2,3-b]pyridine-4,6-dione
2,5-difluoro-3-(3-fluoro-4-methoxy-phenyl)-5-phenyl-7H-thieno[2,3-b]pyridine-4,6-dione
5-fluoro-3-(4-hydroxyphenyl)-5-phenyl-7H-thieno[2,3-b]pyridine-4,6-dione
5-fluoro-3-(3-hydroxyphenyl)-5-phenyl-7H-thieno[2,3-b]pyridine-4,6-dione
2,5-difluoro-3-(3-methoxyphenyl)-5-phenyl-7H-thieno[2,3-b]pyridine-4,6-dione
2-chloro-5-fluoro-3-(3-fluorophenyl)-5-(m-tolyl)-7H-thieno[2,3-b]pyridine-4,6-dione
3-[2-chloro-5-fluoro-3-(3-fluorophenyl)-4,6-dioxo-7H-thieno[2,3-b]pyridin-5-yl]benzonitrile
2-chloro-5-fluoro-3-(3-fluorophenyl)-5-(3-pyridyl)-7H-thieno[2,3-b]pyridine-4,6-dione
2-chloro-5-fluoro-3-(2-hydroxy-3-methyl-phenyl)-5-phenyl-7H-thieno[2,3-b]pyridine-4,6-dione
2-chloro-5-fluoro-3-(4-fluoro-2-hydroxy-phenyl)-5-(3-fluorophenyl)-7H-thieno[2,3-b]pyridine-4,6-dione
2,5-dichloro-3-(4-fluoro-2-hydroxy-phenyl)-5-phenyl-7H-thieno[2,3-b]pyridine-4,6-dione
3-[2-chloro-3-(3,4-dimethylphenyl)-5-fluoro-4,6-dioxo-7H-thieno[2,3-b]pyridin-5-yl]benzonitrile
2-chloro-5-fluoro-3-(4-fluoro-2-hydroxy-phenyl)-5-(4-methylsulfonylphenyl)-7H-thieno[2,3-b]pyridine-4,6-dione
2-chloro-5-(3,4-dimethoxyphenyl)-5-fluoro-3-(4-fluoro-2-hydroxy-phenyl)-7H-thieno[2,3-b]pyridine-4,6-dione
2-chloro-5-fluoro-3-(5-fluoro-2-hydroxy-phenyl)-5-phenyl-7H-thieno[2,3-b]pyridine-4,6-dione
2,5-dichloro-3,5-diphenyl-7H-thieno[2,3-b]pyridine-4,6-dione
2-chloro-3-(4-ethyl-2-hydroxy-phenyl)-5-fluoro-5-phenyl-7H-thieno[2,3-b]pyridine-4,6-dione
3-[2-chloro-5-fluoro-3-(4-fluoro-2-hydroxy-phenyl)-4,6-dioxo-7H-thieno[2,3-b]pyridin-5-yl]benzonitrile
2-chloro-5-fluoro-3-(4-fluoro-2-hydroxy-phenyl)-5-(4-methoxy-3-methyl-phenyl)-7H-thieno[2,3-b]pyridine-4,6-dione
2-chloro-5-fluoro-3-(4-fluoro-2-hydroxy-phenyl)-5-(3-thienyl)-7H-thieno[2,3-b]pyridine-4,6-dione
2-chloro-5-fluoro-3-(3-fluoro-2-hydroxy-4-methyl-phenyl)-5-(4-fluorophenyl)-7H-thieno[2,3-b]pyridine-4,6-dione
2-chloro-3-(4-fluoro-2-hydroxy-phenyl)-5-methoxy-5-phenyl-7H-thieno[2,3-b]pyridine-4,6-dione
2,5-dichloro-3-(3-fluoro-2-hydroxy-4-methyl-phenyl)-5-phenyl-7H-thieno[2,3-b]pyridine-4,6-dione
2,5-dichloro-3-(4-fluoro-2-hydroxy-3-methyl-phenyl)-5-phenyl-7H-thieno[2,3-b]pyridine-4,6-dione.

Preparation of Compounds of Formula (1)

The compounds of the present invention may be prepared in a number of methods well known to those skilled in the art, including, but not limited to, those described below, or through modifications of these methods by applying standard techniques known to those skilled in the art of organic synthesis. All processes disclosed in association with the present invention are contemplated to be practiced on any scale, including milligram, gram, multigram, kilogram, multikilogram or commercial industrial scale.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from active starting materials or by deliberate chiral synthesis of target centers.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, potassium tertiobutylate, sodium tertioamylate, triethylamine, potassium hexamethyldisilazide, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethylformamide; alcohols such as ethanol and methanol and ethers, such as diethyl ether, dioxane and tetrahydrofuran. The reactions can take place over a wide range of temperatures. In general, we find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

Compounds of formula (1) where R3 is a halogen atom and R4 is not a halogen atom could be prepared using compounds of formula (2):

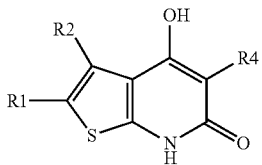

wherein R1, R2 and R4 have the meaning previously described and a reagent known to be a halogen donor such as but not limited to N-chlorosuccinimide (NCS), N-bromosuccinimide (NBS) or selectfluor™ (1-Chloromethyl-4-Fluoro-1,4-Diazoniabicyclo[2.2.2]Octane Bis-(Tetrafluoroborate)). Compounds of formula (2) could be synthesized (for example) using methodology described in U.S. Pat. No. 7,119,205 or WO2009124636.

Compounds of formula (1) where neither of R3 and R4 is a halogen atom could be obtained from compounds of formula (3)

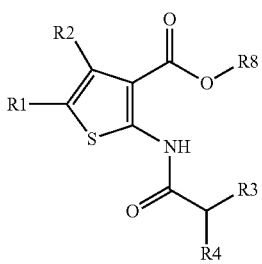

wherein R1, R2, R3 and R4 have the meaning previously described wherein R8 is methyl or ethyl and a base such as, but not limited to, potassium hexamethyldisilazide or sodium hydride.

Compounds of formula (3) could be obtained from the reaction between compounds of formula (4) and compounds of formula (5):

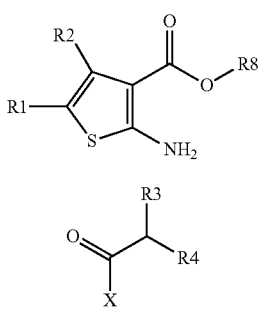

wherein R1, R2, R3, R4 and R8 have the meaning previously described wherein X is OH or a halogen atom (such as Cl or Br).

When X is OH, a carbodiimide coupling agent is needed, such as but not limited to HBTU (see the following internet link for in depth description: http://chemicalland21.com/life-science/phar/HBTU.htm).

Compounds of formula (4) are commercially available (chemos Gmbh, Fluorochem, Acros, Interchim) or easily prepared by a person skilled in the Art by a Gewald reaction described in Journal Heterocycle Chemistry, vol. 36, page 333, 1999.

Pharmaceutical Salts and Other Forms

The compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of formula (1) are for most prepared by conventional methods. If the compound of formula (1) contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of formula (1) are likewise included. In the case of some compounds of formula (1), acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of formula (1) include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-menioned salts, preference is given to ammonium; the alkali metal salts sodium and potassium, and the alkaline earth metal salts calcium and magnesium. Salts of the compounds of the formula (1) which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1$-$C_4)$alkyl halides, for example methyl, ethyl, isopropyl and tert-butyl chloride, bromide and iodide; di$(C_1$-$C_4)$ alkyl sulfates, for example dimethyl, diethyl and diamyl sulfate; $(C_{10}$-$C_{18})$alkyl halides, for example decyl, dodecyl, lauryl, myristyl and stearyl chloride, bromide and iodide; and aryl $(C_1$-$C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula (1) are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of compounds of formula (1) are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salts forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of formula (1) in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Compounds of formula (1) according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

For chiral resolution of the racemates, the following acids and amines can be used:

As examples, the following chiral acids can be used: (+)-D-di-O-benzoyltartaric acid, (−)-L-di-O-benzoyltartaric acid, (−)-L-di-O,O'-p-toluoyl-L-tartaric acid, (+)-D-di-O,O'-p-toluoyl-L-tartaric acid, (R)-(+)-malic acid, (S)-(−)-malic acid, (+)-camphoric acid, (−)-camphoric acid, R-(−)1,1'-binaphtalen-2,2'-diyl hydrogenophosphonic, (+)-camphanic acid, (−)-camphanic acid, (S)-(+)-2-phenylpropionic acid, (R)-(+)-2-phenylpropionic acid, D-(−)-mandelic acid, L-(+)-mandelic acid, D-tartaric acid, L-tartaric acid, or any mixture of them.

As examples, the following chiral amines can be used: quinine, brucine, (S)-1-(benzyloxymethyl)propylamine (III), (−)-ephedrine, (4S,5R)-(+)-1,2,2,3,4-tetramethyl-5-phenyl-1,3-oxazolidine, (R)-1-phenyl-2-p-tolylethylamine, (S)-phenylglycinol, (−)-N-methylephedrine, (+)-(2S,3R)-4-dimethylamino-3-methyl-1,2-diphenyl-2-butanol, (S)-phenylglycinol, (S)-α-methylbenzylamine or any mixture of them.

The present invention also relates to the compounds of the invention for use in a method of treatment of a subject, in particular of treatment of diabetes, metabolic syndrome, obesity, inflammation, cancer or cardiovascular diseases.

The invention furthermore relates to a pharmaceutical composition comprising at least one compound according to the invention in a pharmaceutically acceptable support.

A further object of this invention is a method for treating diseases regulated by activation of AMPK, more specifically diabetes, metabolic syndrome, obesity, inflammation, cancer or cardiovascular diseases, the method comprising administering to a subject in need thereof an effective amount of a compound of the invention.

The invention furthermore relates to the use of compounds of the invention for the preparation of a pharmaceutical composition, in particular for the treatment of diabetes, metabolic syndrome, obesity, inflammation, cancer or cardiovascular diseases.

The pharmaceutical composition according to the invention may be prepared by any conventional method. Compounds of the invention can be converted into a suitable dosage form here together with at least one solid, liquid and/or semi-liquid excipient or adjuvant and, if desired, in combination with one or more further active ingredients.

The term "pharmaceutically acceptable support" refers to carrier, adjuvant, or excipient acceptable to the subject from a pharmacological/toxicological point of view and to the manufacturing pharmaceutical chemist from a physical/chemical point of view regarding to composition, formulation, stability, subject acceptance and bioavailability.

The term "carrier", "adjuvant", or "excipient" refers to any substance, not itself a therapeutic agent, that is added to a pharmaceutical composition to be used as a carrier, adjuvant, and/or diluent for the delivery of a therapeutic agent to a subject in order to improve its handling or storage properties or to permit or facilitate formation of a dosage unit of the composition into a discrete article. The pharmaceutical compositions of the invention, either individually or in combination, can comprise one or several agents or vehicles chosen among dispersants, solubilisers, stabilisers, preservatives, etc.

The term "treatment" or "treating" refers to therapy, prevention and prophylaxis of a disorder which can be potentially regulated by activation of AMPK, in particular diabetes, metabolic syndrome, obesity, inflammation, cancer or cardiovascular diseases. The treatment involves the administration of a compound or pharmaceutical composition to a subject having a declared disorder to cure, delay, or slow down the progress, thus improving the condition of patients. The treatment may be also administered to healthy subjects that are at risk of developing a disorder, in particular diabetes, metabolic syndrome, obesity, inflammation, cancer or cardiovascular diseases.

Within the context of the invention, the term "subject" means a mammal and more particularly a human. The subjects to be treated according to the invention can be appropriately selected on the basis of several criteria associated to the disease such as previous drug treatments, associated pathologies, genotype, exposure to risk factors, viral infection, as well as any other relevant biomarker that can be evaluated by means of immunological, biochemical, enzymatic, chemical, or nucleic acid detection method. In a particular embodiment, the subject is an overweighed patient (in particular an overweighed prediabetic patient) or obese patient suffering from atherogenic dyslipidemia. Indeed, these patients are at risk of developing a disease which can be potentially regulated by activation of AMPK, in particular diabetes, metabolic syndrome, obesity, inflammation, cancer or cardiovascular diseases.

Pharmaceutical compositions can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical compositions can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical compositions of this type can be prepared using a process which is generally known in the pharmaceutical art.

Pharmaceutical compositions can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such compositions can be prepared using all processes known in the pharmaceutical art by, for example, combining the active ingredient with the excipient(s) or adjuvant(s).

Pharmaceutical compositions adapted for oral administration can be administered as separate units, such as, for example, capsules or tablets; powders or granules; solutions or suspensions in aqueous or non-aqueous liquids; edible foams or foam foods; or emulsions, such as oil-in-water liquid emulsions or water-in-oil liquid emulsions.

Thus, for example, in the case of oral administration in the form of a tablet or capsule, the active ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compounds. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical compositions adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compositions adapted for topical administration can be formulated as ointments, creams, suspensions, lotions, powders, solutions, pastes, gels, sprays, aerosols or oils.

For the treatment of the eye or other external tissue, for example mouth and skin, the compositions are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical compositions adapted for topical application to the eye include eye drops, in which the active ingredient is dissolved or suspended in a suitable carrier, in particular an aqueous solvent.

Pharmaceutical compositions adapted for topical application in the mouth encompass lozenges, pastilles and mouthwashes.

Pharmaceutical compositions adapted for rectal administration can be administered in the form of suppositories or enemas.

Pharmaceutical compositions adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical compositions adapted for administration by inhalation encompass finely particulate dusts or mists, which can be generated by various types of pressurised dispensers with aerosols, nebulisers or insufflators.

Pharmaceutical compositions adapted for vaginal administration can be administered as pessaries, tampons, creams, gels, pastes, foams or spray formulations.

Pharmaceutical compositions adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the compositions may also comprise other agents usual in the art with respect to the particular type of formulation; thus, for example, formulations which are suitable for oral administration may comprise flavours.

A therapeutically effective amount of a compound of the present invention depends on a number of factors, including, for example, the age and weight of the human or animal, the precise disease condition which requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The following examples illustrate the invention without, however, limiting it. The starting materials used are known products or products prepared according to known procedures. The percentages are expressed on a weight basis, unless otherwise mentioned.

EXAMPLES

The compounds were characterised especially via the following analytical techniques:
NMR spectra were acquired using a Bruker Avance DPX 300 MHz NMR spectrometer;
Masses (MS) were determined by HPLC coupled to an Agilent Series 1100 mass detector.

Example 1

2-chloro-3-(3-methoxyphenyl)-5-methyl-5-(m-tolyl)-7H-thieno[2,3-b]pyridine-4,6-dione Step 1: 1-(3-methoxyphenyl)ethanone (5 mL) was dissolved in acetic acid (50 mL). Ethyl cyanoacate (4.69 mL) was added. After a few minutes of stirring, hexamethyldisilazane (15.35 mL) was added dropwise and the whole mixture was heated at 90° C. during 6 hours. At that point, most of the solvent was removed under reduced pressure and the crude oil was taken up into ethyl acetate. The solution was washed with sodium bicarbonate solution, water and brine. Organic solution was dryed over sodium sulfate and ethyl acetate removed under reduced pressure. The crude oil (9.3 g) was purified over silica (cyclohexane/dichloromethane 100/0 to 50/50). An orange oil (6.51 g, 67%) was recovered.
LC: 5.06 min
MS: 244.1 (M−1)
Step 2: Previous oil (6.51 g) was dissolved into ethanol (100 mL). Morpholine (2.43 mL) and sulfur (1.9 g) were added and the mixture was heated to reflux during 3 hours. Inorganic materials were filtered off and the ethanol solution concentred under reduced pressure. The thick dark oil was taken up into ethyl acetate, washed with water, 1M hydrochloric acid solution and brine then dried over sodium sulfate. Ethyl acetate was removed under reduced pressure and the crude purified over silica (petroleum ether/dichloromethane 70/30 to 20/80). A yellow solid (4.18 g, 60%) was recovered.
LC: 5.10 min
MS: 278 (M+1)
Step 3: Previous solid (4.15 g) was dissolved in dichloromethane (50 mL) and the solution was cooled to −10° C. N-chlorosuccinimide (2 g) was added portionwise and the mixture was stirred during 1 hour at 5° C. Organic solution was washed 3 times with water, dried over sodium sulfate and the solvent removed under reduced pressure. Thick dark oil (5.09 g, 95%) was obtained.
LC: 5.47 min
MS: 311.9 (M+1)
Step 4: To previous oil (500 mg) in tetrahydrofurane (15 mL) was added potassium carbonate (430 mg) then dropwise a tetrahydrofurane solution (5 mL) of 2-(m-tolyl)propanoyl chloride (340 mg, intermediate 1). After 5 hours of stirring, water was added and ethyl acetate extraction was performed. Organic solution was washed with saturated sodium bicarbonate solution and brine, then dried over sodium sulfate. The solvent was removed under reduced pressure and the remaining dark oil (835 mg) was purified over silica (petroleum ether/dichloromethane 50/50). A yellow oil (548 mg, 71%) was recovered.
LC: 6.70 min
MS: 458 (M+1)
Step 5: To a mixture of potassium hexamethyldisilylazide (880 mg) into tetrahydrofurane (7 mL) was added dropwise a solution of previous oil (518 mg) into tetrahydrofurane (3 mL). After one hour, the reaction mixture was quenched with water and pH was adjusted with acetic acid (around pH4). Extraction by ethyl acetate was done and the organic phase was washed with saturated sodium bicarbonate solution and brine. Organic phase was dried over sodium sulphate and ethyl acetate was removed under reduced pressure. The remaining orange oil was purified over silica (heptanes/ethyl acetate 85/15 to 80/20). Yellow oil (139 mg, 30%) was obtained.
LC: 5.47 min
MS: 412 (M+1)
1HNMR: 1.60 (s, 3H), 2.35 (s, 3H), 3.80 (s, 3H), 6.65-7.35 (m, 8H), 11.85 (s, 1H)

Example 2

2-chloro-5-methoxy-3,5-diphenyl-7H-thieno[2,3-b]pyridine-4,6-dione

Step 1: To a solution of commercially available ethyl 2-amino-4-phenyl-thiophene-3-carboxylate (5 g) in chloroform (180 mL) cooled to −5° C. was added N-chlorosuccinimide (2.68 g) portionwise. After 2 hours of stirring at 5° C., the solvent was removed under reduced pressure. The remaining brown oil was purified over silica (petroleum ether/dichloromethane 70/30) affording a dark red solid (5.13 g, 89%).
LC: 5.61 min
MS: 282 (M+1)
Step 2: To previous solid (1.7 g) in tetrahydrofurane (6 mL) was added potassium carbonate (1.66 g) then dropwise a tetrahydrofurane solution of 2-methoxy-2-phenyl-acetyl chloride (6 mmol, intermediate 2). After 20 hours of stirring, water, acetic acid and ethyl acetate were added. Organic solution was washed twice with brine, then dried over sodium sulfate. The solvent was removed under reduced pressure and the crude was purified over silica (dichloromethane/cyclohexane 80/20). A purple solid (2.1 g, 80%) was recovered.
LC: 4.46 min
MS: 430 (M−1)
Step 3: To a solution of potassium hexamethyldisilylazide (3.38 g) in tetrahydrofurane (12 mL) cooled at 15° C. was added dropwise previous compound (1.82 g) in tetrahydrofurane solution (12 mL). After 1.5 hour of stirring, the mixture was cooled to 0° C. and quenched with water (50 mL). pH was adjusted to 4 with acetic acid and an extraction with ethyl acetate was done. Organic phase was washed with brine (twice) then dried over sodium sulfate. The solvent was removed under reduced pressure and the crude was purified over silica (dichloromethane/acetone 98/2). 550 mg (52%) of pure compound were collected.

LC: 5.05 min
MS: 384 (M+1)
1HNMR: 3.28 (s, 3H), 7.05-7.50 (m, 10H), 12.00 (s, 1H)

Example 3

5-fluoro-2-methyl-3,5-diphenyl-7H-thieno[2,3-b]pyridine-4,6-dione

Step 1: To a solution of 4-hydroxy-2-methyl-3,5-diphenyl-7H-thieno[2,3-b]pyridin-6-one (100 mg) in acetonitrile (3 mL) was added selecfluor™ (106.3 mg). After 20 hours of stirring, the reaction mixture was quenched with water and extracted with ethyl acetate. Organic phase was dried over sodium sulfate and the solvent removed under reduced pressure. The crude was purified over silica (ethyl acetate) affording 12 mg (11%) of pure compound.

LC: 4.94 min
MS: 350.0 (M−1)
1HNMR: 2.20 (s, 3H), 7.08-8.15 (m, 10H), 12.30 (s, 1H)

Examples 4 and 5

3-[5-fluoro-3-(2-methoxy-4-methyl-phenyl)-4,6-dioxo-7H-thieno[2,3-b]pyridine-5-yl]benzonitrile (A)

3-[2,5-difluoro-3-(2-methoxy-4-methyl-phenyl)-4,6-dioxo-7H-thieno[2,3-b]pyridine-5-yl]benzonitrile (B)

Step 1: To a solution of 3-[4-hydroxy-3-(2-methoxy-4-methyl-phenyl)-6-oxo-7H-thieno[2,3-b]pyridin-5-yl]benzonitrile (150 mg) in acetonitrile (3 mL) was added selecfluor™ (137 mg). After 20 hours of stirring, the reaction mixture was quenched with water and extracted with ethyl acetate. Organic phase was dried over sodium sulfate and the solvent removed under reduced pressure. The crude was purified over silica (ethyl acetate). Both compounds (A: 5.2 mg and B: 4.5 mg) were isolated after a preparative HPLC.

(A)
LC: 4.78 min
MS: 405 (M−1)
1HNMR: 2.30 (s, 3H), 3.20 (s, 3H), 6.75-8.05 (m, 8H), 12.24 (s, 1H)

(B)
LC: 4.96 min
MS: 423.0 (M−1)
1HNMR: 2.35 (s, 3H), 3.11 (s, 3H), 6.79-8.03 (m, 7H), 12.07 (s, 1H)

Example 6

3,5,5-triphenyl-7H-thieno[2,3-b]pyridine-4,6-dione

Step 1: To a solution of commercially available ethyl 2-amino-4-phenyl-thiophene-3-carboxylate (1.56 g) in dioxane (10 mL) was added dropwise 2,2-diphenylacetyl chloride (intermediate 3, 7.07 mmol). After 20 hours of stirring, the reaction mixture was quenched with water and extracted with ethyl acetate. Organic phase was washed with a saturated sodium bicarbonate solution, water and brine then dried over sodium sulfate and the solvent removed under reduced pressure to afford orange oil (1.64 g, 58%).

LC: 10.91 min
MS: 442.1 (M+1)

Step 2: To a solution of potassium hexamethyldisilylazide (1.52 g) in tetrahydrofurane (5 mL) was added dropwise previous compound (0.80 g) in tetrahydrofurane solution (10 mL). After 1 hour of stirring, hydrochloric acid solution (1M) was added until neutral pH and an extraction with ethyl acetate was done. Organic phase was washed with water and brine then dried over sodium sulfate. The solvent was removed under reduced pressure and the crude was purified over silica (petroleum ether/dichloromethane 60/40) affording a pure white solid (372 mg, 51%).

LC: 8.70
MS: 396.0 (M+1)
1HNMR: 6.99-7.41 (m, 16H)

Intermediate 1, Intermediate 2 and Intermediate 3

Corresponding carboxylic acid was dissolved in dichloromethane. Oxalyl chloride (3 eq) and a drop of dimethylformamide were added. After 1 hour of stirring, solvent was removed under reduced pressure and the acyl chloride was used without any further purification.

The following compounds in Table (1) can be obtained analogously.

TABLE (1)

| No | name | MS |
|---|---|---|
| 1 | 5-methyl-3,5-diphenyl-7H-thieno[2,3-b]pyridine-4,6-dione | 334 (M + 1) |
| 2 | 2-chloro-5-methyl-3,5-diphenyl-7H-thieno[2,3-b]pyridine-4,6-dione | 368 (M + 1) |
| 3 | 2-chloro-3-(2-fluoro-4-methoxy-phenyl)-5-methyl-5-phenyl-7H-thieno[2,3-b]pyridine-4,6-dione | 416 (M + 1) |
| 4 | 3-(3-fluoro-2-methoxy-4-methyl-phenyl)-5-methyl-5-(p-tolyl)-7H-thieno[2,3-b]pyridine-4,6-dione | 410 (M + 1) |
| 5 | 2-chloro-3-(3-fluoro-2-methoxy-4-methyl-phenyl)-5-methyl-5-phenyl-7H-thieno[2,3-b]pyridine-4,6-dione | 430 (M + 1) |
| 6 | 2-chloro-3-(4-fluoro-2-methoxy-phenyl)-5-methyl-5-phenyl-7H-thieno[2,3-b]pyridine-4,6-dione | 416 (M + 1) |
| 7 | 2-chloro-3-(1-hydroxy-2-naphthyl)-5-methyl-5-phenyl-7H-thieno[2,3-b]pyridine-4,6-dione | 434 (M + 1) |
| 8 | 3-(1-hydroxy-2-naphthyl)-5-methyl-5-phenyl-7H-thieno[2,3-b]pyridine-4,6-dione | 400 (M + 1) |
| 9 | 3,5,5-triphenyl-7H-thieno[2,3-b]pyridine-4,6-dione | 396 (M + 1) |
| 10 | 5-benzyl-3,5-diphenyl-7H-thieno[2,3-b]pyridine-4,6-dione | 410 (M + 1) |
| 11 | 5-ethyl-3,5-diphenyl-7H-thieno[2,3-b]pyridine-4,6-dione | 348 (M + 1) |
| 12 | 2-chloro-3-(3-ethoxy-4-fluoro-2-methoxy-phenyl)-5-methyl-5-phenyl-7H-thieno[2,3-b]pyridine-4,6-dione | 460 (M + 1) |
| 13 | 2-chloro-3-(3,4-difluoro-2-methoxy-phenyl)-5-methyl-5-phenyl-7H-thieno[2,3-b]pyridine-4,6-dione | 434 (M + 1) |
| 14 | 3-(3,4-difluoro-2-hydroxy-phenyl)-5-methyl-5-phenyl-7H-thieno[2,3-b]pyridine-4,6-dione | 384 (M − 1) |
| 15 | 2-chloro-3-(4-fluoro-2-hydroxy-phenyl)-5-(4-methoxyphenyl)-5-methyl-7H-thieno[2,3-b]pyridine-4,6-dione | 432 (M + 1) |
| 16 | 3-(4-ethyl-2-methoxy-phenyl)-5-methyl-5-phenyl-7H-thieno[2,3-b]pyridine-4,6-dione | 392 (M + 1) |
| 17 | 5-(4-ethoxyphenyl)-3-(2-fluoro-4-methyl-phenyl)-5-methyl-7H-thieno[2,3-b]pyridine-4,6-dione | 410 (M + 1) |
| 18 | 5,5-dimethyl-3-phenyl-7H-thieno[2,3-b]pyridine-4,6-dione | 272 (M + 1) |
| 19 | 5-(4-ethoxyphenyl)-3-(4-fluoro-2-hydroxy-3-methyl-phenyl)-2,5-dimethyl-7H-thieno[2,3-b]pyridine-4,6-dione | 440 (M + 1) |
| 20 | 2-chloro-5-fluoro-3,5-diphenyl-7H-thieno[2,3-b]pyridine-4,6-dione | 370 (M − 1) |
| 21 | 3-(4-chloro-2-methoxy-phenyl)-5-(4-ethoxyphenyl)-5-methyl-7H-thieno[2,3-b]pyridine-4,6-dione | 442 (M + 1) |
| 22 | 2-chloro-5-(4-ethoxyphenyl)-3-(2-fluoro-4-methyl-phenyl)-5-methyl-7H-thieno[2,3-b]pyridine-4,6-dione | 444 (M + 1) |

TABLE (1)-continued

| No | name | MS |
|---|---|---|
| 23 | 5-(4-ethoxyphenyl)-3-(3-fluoro-2-hydroxy-4-methyl-phenyl)-5-methyl-7H-thieno[2,3-b]pyridine-4,6-dione | 426 (M + 1) |
| 24 | 3-(3-fluoro-2-hydroxy-4-methyl-phenyl)-5-(4-hydroxy-phenyl)-5-methyl-7H-thieno[2,3-b]pyridine-4,6-dione | 398 (M + 1) |
| 25 | 5-fluoro-3-(4-fluoro-2-hydroxy-phenyl)-5-phenyl-7H-thieno[2,3-b]pyridine-4,6-dione | 370 (M − 1) |
| 26 | 2-chloro-3-(4-fluorophenyl)-5-methyl-5-phenyl-7H-thieno[2,3-b]pyridine-4,6-dione | 386 (M + 1) |
| 27 | 2-chloro-5-(3-fluorophenyl)-5-methyl-3-phenyl-7H-thieno[2,3-b]pyridine-4,6-dione | 384 (M − 1) |
| 28 | 2-chloro-5-(2-fluorophenyl)-5-methyl-3-phenyl-7H-thieno[2,3-b]pyridine-4,6-dione | 386 (M + 1) |
| 29 | 2-chloro-3-(3-fluorophenyl)-5-methyl-5-phenyl-7H-thieno[2,3-b]pyridine-4,6-dione | 384 (M − 1) |
| 30 | 2-chloro-3-(2-fluorophenyl)-5-methyl-5-phenyl-7H-thieno[2,3-b]pyridine-4,6-dione | 384 (M − 1) |
| 31 | 2-chloro-5-methyl-3-phenyl-5-(p-tolyl)-7H-thieno[2,3-b]pyridine-4,6-dione | 382 (M + 1) |
| 32 | 2-chloro-5-(4-fluorophenyl)-5-methyl-3-phenyl-7H-thieno[2,3-b]pyridine-4,6-dione | 384 (M − 1) |
| 33 | 2-chloro-5-methyl-5-(m-tolyl)-3-phenyl-7H-thieno[2,3-b]pyridine-4,6-dione | 380 (M − 1) |
| 34 | 2-chloro-5-methyl-5-phenyl-3-(p-tolyl)-7H-thieno[2,3-b]pyridine-4,6-dione | 382 (M + 1) |
| 35 | 2-chloro-5-(4-methoxyphenyl)-5-methyl-3-phenyl-7H-thieno[2,3-b]pyridine-4,6-dione | 398 (M + 1) |
| 36 | 2-chloro-3-(4-methoxyphenyl)-5-methyl-5-phenyl-7H-thieno[2,3-b]pyridine-4,6-dione | 398 (M + 1) |
| 37 | 2-chloro-3-(3-fluorophenyl)-5-(4-fluorophenyl)-5-methyl-7H-thieno[2,3-b]pyridine-4,6-dione | 404 (M + 1) |
| 38 | 2-chloro-5-(3-methoxyphenyl)-5-methyl-3-phenyl-7H-thieno[2,3-b]pyridine-4,6-dione | 398 (M + 1) |
| 39 | 2-chloro-5-(4-fluorophenyl)-3-(4-methoxyphenyl)-5-methyl-7H-thieno[2,3-b]pyridine-4,6-dione | 416 (M + 1) |
| 40 | 2-chloro-3-(3-methoxyphenyl)-5-methyl-5-phenyl-7H-thieno[2,3-b]pyridine-4,6-dione | 398 (M + 1) |
| 41 | 2-chloro-3-(3-methoxyphenyl)-5-methyl-5-(p-tolyl)-7H-thieno[2,3-b]pyridine-4,6-dione | 412 (M + 1) |
| 42 | 2-chloro-5-(4-fluorophenyl)-3-(3-methoxyphenyl)-5-methyl-7H-thieno[2,3-b]pyridine-4,6-dione | 416 (M + 1) |
| 43 | 2-chloro-3-(3-methoxyphenyl)-5-(4-methoxyphenyl)-5-methyl-7H-thieno[2,3-b]pyridine-4,6-dione | 428 (M + 1) |
| 44 | 2-chloro-3-(3-methoxyphenyl)-5-methyl-5-(m-tolyl)-7H-thieno[2,3-b]pyridine-4,6-dione | 412 (M + 1) |
| 45 | 2-chloro-5-(3-fluorophenyl)-5-methyl-3-(p-tolyl)-7H-thieno[2,3-b]pyridine-4,6-dione | 400 (M + 1) |
| 46 | 2-chloro-5-fluoro-3-(4-fluoro-2-hydroxy-phenyl)-5-phenyl-7H-thieno[2,3-b]pyridine-4,6-dione | 404 (M − 1) |
| 47 | 2-chloro-5-(2-fluorophenyl)-5-methyl-3-(o-tolyl)-7H-thieno[2,3-b]pyridine-4,6-dione | 400 (M + 1) |
| 48 | 2-chloro-5-methoxy-3,5-diphenyl-7H-thieno[2,3-b]pyridine-4,6-dione | 384 (M + 1) |
| 49 | 2-chloro-3,5-bis(4-fluorophenyl)-5-methyl-7H-thieno[2,3-b]pyridine-4,6-dione | 404 (M + 1) |
| 50 | 2-chloro-3-(4-fluorophenyl)-5-methyl-5-(p-tolyl)-7H-thieno[2,3-b]pyridine-4,6-dione | 400 (M + 1) |
| 51 | 2-chloro-5-(3-fluorophenyl)-3-(4-fluorophenyl)-5-methyl-7H-thieno[2,3-b]pyridine-4,6-dione | 404 (M + 1) |
| 52 | 2-chloro-5-(4-fluorophenyl)-3-(2-methoxyphenyl)-5-methyl-7H-thieno[2,3-b]pyridine-4,6-dione | 416 (M + 1) |
| 53 | 2-chloro-3-(4-fluorophenyl)-5-methyl-5-(4-methoxyphenyl)-7H-thieno[2,3-b]pyridine-4,6-dione | 416 (M + 1) |
| 54 | 2-chloro-3-(4-fluorophenyl)-5-methyl-5-(4-methylsulfonylphenyl)-7H-thieno[2,3-b]pyridine-4,6-dione | 462 (M − 1) |
| 55 | 2-chloro-5-(2-methoxyphenyl)-3-(4-fluorophenyl)-5-methyl-7H-thieno[2,3-b]pyridine-4,6-dione | 402 (M − 1) |
| 56 | 2-chloro-3-(2-methoxyphenyl)-5-methyl-5-(m-tolyl)-7H-thieno[2,3-b]pyridine-4,6-dione | 412 (M + 1) |
| 57 | 2-chloro-5-(4-fluorophenyl)-5-methyl-3-(p-tolyl)-7H-thieno[2,3-b]pyridine-4,6-dione | 400 (M + 1) |
| 58 | 2-chloro-5-(3-methoxyphenyl)-5-methyl-3-(o-tolyl)-7H-thieno[2,3-b]pyridine-4,6-dione | 412 (M + 1) |
| 59 | 2-chloro-5-methyl-5-(m-tolyl)-3-(o-tolyl)-7H-thieno[2,3-b]pyridine-4,6-dione | 396 (M + 1) |
| 60 | 2-chloro-3-(3-fluorophenyl)-5-methyl-5-(p-tolyl)-7H-thieno[2,3-b]pyridine-4,6-dione | 398 (M − 1) |
| 61 | 2-chloro-3,5-bis(3-methoxyphenyl)-5-methyl-7H-thieno[2,3-b]pyridine-4,6-dione | 428 (M + 1) |
| 62 | 2-chloro-5-(3-fluorophenyl)-3-(3-methoxyphenyl)-5-methyl-7H-thieno[2,3-b]pyridine-4,6-dione | 416 (M + 1) |
| 63 | 2-chloro-3-(4-fluorophenyl)-5-(3-methoxyphenyl)-5-methyl-7H-thieno[2,3-b]pyridine-4,6-dione | 416 (M + 1) |
| 64 | 2-chloro-3-(4-fluorophenyl)-5-methyl-5-(3-methylsulfonylphenyl)-7H-thieno[2,3-b]pyridine-4,6-dione | 462 (M − 1) |
| 65 | 2-chloro-3-(2-methoxyphenyl)-5-methyl-5-(p-tolyl)-7H-thieno[2,3-b]pyridine-4,6-dione | 412 (M + 1) |
| 66 | 2-chloro-5-(3-fluorophenyl)-3-(2-methoxyphenyl)-5-methyl-7H-thieno[2,3-b]pyridine-4,6-dione | 416 (M + 1) |
| 67 | 2-chloro-3-(2-methoxyphenyl)-5-(4-methoxyphenyl)-5-methyl-7H-thieno[2,3-b]pyridine-4,6-dione | 428 (M + 1) |
| 68 | 2-chloro-3-(2-methoxyphenyl)-5-(3-methoxyphenyl)-5-methyl-7H-thieno[2,3-b]pyridine-4,6-dione | 428 (M + 1) |
| 69 | 2-chloro-5-(2-fluorophenyl)-3-(2-methoxyphenyl)-5-methyl-7H-thieno[2,3-b]pyridine-4,6-dione | 416 (M + 1) |
| 70 | 5-fluoro-2-methyl-3,5-diphenyl-7H-thieno[2,3-b]pyridine-4,6-dione | 350 (M − 1) |
| 71 | 2-chloro-5-fluoro-5-phenyl-3-(3-pyridyl)-7H-thieno[2,3-b]pyridine-4,6-dione | 371 (M − 1) |
| 72 | 2-chloro-5-fluoro-3-(4-hydroxyphenyl)-5-phenyl-7H-thieno[2,3-b]pyridine-4,6-dione | 386 (M − 1) |
| 73 | 2-chloro-5-fluoro-3-(2-fluorophenyl)-5-phenyl-7H-thieno[2,3-b]pyridine-4,6-dione | 388 (M − 1) |
| 74 | 2-chloro-5-fluoro-3-(2-fluoro-4-methoxy-phenyl)-5-phenyl-7H-thieno[2,3-b]pyridine-4,6-dione | 418 (M − 1) |
| 75 | 2-chloro-3-(2-fluorophenyl)-5-methyl-5-(p-tolyl)-7H-thieno[2,3-b]pyridine-4,6-dione | 400 (M + 1) |
| 76 | 2-chloro-3-(2-fluorophenyl)-5-(3-methoxyphenyl)-5-methyl-7H-thieno[2,3-b]pyridine-4,6-dione | 416 (M + 1) |
| 77 | 2-chloro-5-fluoro-3-(3-fluoro-4-hydroxy-phenyl)-5-phenyl-7H-thieno[2,3-b]pyridine-4,6-dione | 404 (M − 1) |
| 78 | 5-fluoro-5-(2-methoxyphenyl)-2-methyl-3-phenyl-7H-thieno[2,3-b]pyridine-4,6-dione | 380 (M − 1) |
| 79 | 2-chloro-5-fluoro-3-(m-tolyl)-5-phenyl-7H-thieno[2,3-b]pyridine-4,6-dione | 384 (M − 1) |
| 80 | 2-chloro-5-fluoro-5-phenyl-3-(p-tolyl)-7H-thieno[2,3-b]pyridine-4,6-dione | 384 (M − 1) |
| 81 | 2-chloro-5-fluoro-3-(4-methoxyphenyl)-5-phenyl-7H-thieno[2,3-b]pyridine-4,6-dione | 400 (M − 1) |
| 82 | 2-chloro-5-fluoro-5-(3-methylsulfonylphenyl)-3-phenyl-7H-thieno[2,3-b]pyridine-4,6-dione | 448 (M − 1) |
| 83 | 2-chloro-3-(4-fluorophenyl)-5-methyl-5-(m-tolyl)-7H-thieno[2,3-b]pyridine-4,6-dione | 400 (M + 1) |
| 84 | 2-chloro-3-(2-fluorophenyl)-5-(4-methoxyphenyl)-5-methyl-7H-thieno[2,3-b]pyridine-4,6-dione | 416 (M + 1) |
| 85 | 2-chloro-5-(3-fluorophenyl)-3-(4-methoxyphenyl)-5-methyl-7H-thieno[2,3-b]pyridine-4,6-dione | 416 (M + 1) |
| 86 | 2-chloro-3,5-bis(4-methoxyphenyl)-5-methyl-7H-thieno[2,3-b]pyridine-4,6-dione | 428 (M + 1) |
| 87 | 2-chloro-3-(4-methoxyphenyl)-5-methyl-5-(m-tolyl)-7H-thieno[2,3-b]pyridine-4,6-dione | 412 (M + 1) |
| 88 | 2-chloro-5-(3-methoxyphenyl)-3-(4-methoxyphenyl)-5-methyl-7H-thieno[2,3-b]pyridine-4,6-dione | 428 (M + 1) |
| 89 | 2-chloro-3,5-bis(2-fluorophenyl)-5-methyl-7H-thieno[2,3-b]pyridine-4,6-dione | 404 (M + 1) |
| 90 | 2-chloro-3-(2-fluorophenyl)-5-(3-fluorophenyl)-5-methyl-7H-thieno[2,3-b]pyridine-4,6-dione | 404 (M + 1) |
| 91 | 2-chloro-3-(2-fluorophenyl)-5-(4-fluorophenyl)-5-methyl-7H-thieno[2,3-b]pyridine-4,6-dione | 404 (M + 1) |
| 92 | 2-chloro-3-(2-fluorophenyl)-5-methyl-5-(m-tolyl)-7H-thieno[2,3-b]pyridine-4,6-dione | 400 (M + 1) |
| 93 | 2-chloro-5-fluoro-5-phenyl-3-(4-pyridyl)-7H-thieno[2,3-b]pyridine-4,6-dione | 371 (M − 1) |
| 94 | 2-chloro-5-fluoro-3-(3-methoxyphenyl)-5-phenyl-7H-thieno[2,3-b]pyridine-4,6-dione | 400 (M − 1) |
| 95 | 2-chloro-5-fluoro-3-phenyl-5-[3-(trifluoro-methyl)phenyl]-7H-thieno[2,3-b]pyridine-4,6-dione | 438 (M − 1) |
| 96 | 2-chloro-3-(4-methoxyphenyl)-5-methyl-5-(p-tolyl)-7H-thieno[2,3-b]pyridine-4,6-dione | 412 (M + 1) |
| 97 | 2-chloro-5-fluoro-5-(4-methylsulfonylphenyl)-3-phenyl-7H-thieno[2,3-b]pyridine-4,6-dione | 448 (M − 1) |
| 98 | 2-chloro-5-fluoro-5-(2-methoxyphenyl)-3-phenyl-7H-thieno[2,3-b]pyridine-4,6-dione | 400 (M − 1) |
| 99 | 2-chloro-5-fluoro-3-(4-fluoro-2-hydroxy-phenyl)-5-(2-methoxyphenyl)-7H-thieno[2,3-b]pyridine-4,6-dione | 436 (M + 1) |
| 100 | 5-fluoro-3,5-diphenyl-7H-thieno[2,3-b]pyridine-4,6-dione | 336 (M − 1) |

TABLE (1)-continued

| No | name | MS |
|---|---|---|
| 101 | 2-chloro-3-(2-chlorophenyl)-5-fluoro-5-phenyl-7H-thieno[2,3-b]pyridine-4,6-dione | 404 (M − 1) |
| 102 | 5-fluoro-3-(4-fluoro-2-hydroxy-3-methyl-phenyl)-5-phenyl-7H-thieno[2,3-b]pyridine-4,6-dione | 384 (M − 1) |
| 103 | 2-chloro-3,5-bis(3-fluorophenyl)-5-methyl-7H-thieno[2,3-b]pyridine-4,6-dione | 404 (M + 1) |
| 104 | 2-chloro-5-(2-fluorophenyl)-3-(3-fluorophenyl)-5-methyl-7H-thieno[2,3-b]pyridine-4,6-dione | 404 (M + 1) |
| 105 | 2-chloro-3-(3-fluorophenyl)-5-(3-methoxyphenyl)-5-methyl-7H-thieno[2,3-b]pyridine-4,6-dione | 416 (M + 1) |
| 106 | 2-chloro-3-(3-fluorophenyl)-5-methyl-5-(m-tolyl)-7H-thieno[2,3-b]pyridine-4,6-dione | 400 (M + 1) |
| 107 | 2-chloro-3-(2-methoxyphenyl)-5-methyl-5-phenyl-7H-thieno[2,3-b]pyridine-4,6-dione | 398 (M + 1) |
| 108 | 5-fluoro-3-(4-fluoro-2-hydroxy-3-methyl-phenyl)-5-(4-fluorophenyl)-7H-thieno[2,3-b]pyridine-4,6-dione | 402 (M − 1) |
| 109 | 5-fluoro-3-(4-fluoro-2-hydroxy-phenyl)-5-(p-tolyl)-7H-thieno[2,3-b]pyridine-4,6-dione | 384 (M − 1) |
| 110 | 3-[5-fluoro-3-(2-methoxy-4-methyl-phenyl)-4,6-dioxo-7H-thieno[2,3-b]pyridin-5-yl]benzonitrile | 405 (M − 1) |
| 111 | 3-[2,5-difluoro-3-(2-methoxy-4-methyl-phenyl)-4,6-dioxo-7H-thieno[2,3-b]pyridin-5-yl]benzonitrile | 423 (M − 1) |
| 112 | 5-fluoro-3-(2-hydroxy-6-methoxy-phenyl)-5-phenyl-7H-thieno[2,3-b]pyridine-4,6-dione | 382 (M − 1) |
| 113 | 5-fluoro-3-(3-methoxy-4-methyl-phenyl)-5-phenyl-7H-thieno[2,3-b]pyridine-4,6-dione | 380 (M − 1) |
| 114 | 2,5-difluoro-3-(3-methoxy-4-methyl-phenyl)-5-phenyl-7H-thieno[2,3-b]pyridine-4,6-dione | 398 (M − 1) |
| 115 | 5-fluoro-3-(3-hydroxy-4-methyl-phenyl)-5-phenyl-7H-thieno[2,3-b]pyridine-4,6-dione | 366 (M − 1) |
| 116 | 2,5-difluoro-3-(3-hydroxy-4-methyl-phenyl)-5-phenyl-7H-thieno[2,3-b]pyridine-4,6-dione | 384 (M − 1) |
| 117 | 2-chloro-5-methyl-3-(m-tolyl)-5-(p-tolyl)-7H-thieno[2,3-b]pyridine-4,6-dione | 396 (M + 1) |
| 118 | 5-fluoro-3-(2-methoxy-4-methyl-phenyl)-5-phenyl-7H-thieno[2,3-b]pyridine-4,6-dione | 380 (M − 1) |
| 119 | 2,5-difluoro-3-(2-methoxy-4-methyl-phenyl)-5-phenyl-7H-thieno[2,3-b]pyridine-4,6-dione | 398 (M − 1) |
| 120 | 5-fluoro-3-(3-methylsulfonylphenyl)-5-phenyl-7H-thieno[2,3-b]pyridine-4,6-dione | 414 (M − 1) |
| 121 | 5-fluoro-3-(2-hydroxy-4-methyl-phenyl)-5-phenyl-7H-thieno[2,3-b]pyridine-4,6-dione | 366 (M − 1) |
| 122 | 3-(2,6-difluorophenyl)-5-fluoro-5-phenyl-7H-thieno[2,3-b]pyridine-4,6-dione | 372 (M − 1) |
| 123 | 3-(4-bromo-2-hydroxy-phenyl)-5-fluoro-5-phenyl-7H-thieno[2,3-b]pyridine-4,6-dione | 432 (M − 1) |
| 124 | 3-(4-bromophenyl)-5-fluoro-5-(4-pyridyl)-7H-thieno[2,3-b]pyridine-4,6-dione | 417 (M − 1) |
| 125 | 3-(2-bromophenyl)-5-fluoro-5-phenyl-7H-thieno[2,3-b]pyridine-4,6-dione | 416 (M − 1) |
| 126 | 2-chloro-5-(3-methoxyphenyl)-5-methyl-3-(m-tolyl)-7H-thieno[2,3-b]pyridine-4,6-dione | 412 (M + 1) |
| 127 | 3-(4-bromo-2-methoxy-phenyl)-5-fluoro-5-phenyl-7H-thieno[2,3-b]pyridine-4,6-dione | 446 (M − 1) |
| 128 | 3-(4-bromo-2-methoxy-phenyl)-2,5-difluoro-5-phenyl-7H-thieno[2,3-b]pyridine-4,6-dione | 464 (M − 1) |
| 129 | 5-fluoro-3-(o-tolyl)-5-phenyl-7H-thieno[2,3-b]pyridine-4,6-dione | 352 (M + 1) |
| 130 | 2,5-difluoro-3-(o-tolyl)-5-phenyl-7H-thieno[2,3-b]pyridine-4,6-dione | 368 (M − 1) |
| 131 | 5-fluoro-3-phenyl-5-[3-(trifluoromethyl)phenyl]-7H-thieno[2,3-b]pyridine-4,6-dione | 404 (M − 1) |
| 132 | 2,5-difluoro-3-phenyl-5-[3-(trifluoromethyl)phenyl]-7H-thieno[2,3-b]pyridine-4,6-dione | 422 (M − 1) |
| 133 | 5-fluoro-3-phenyl-5-[4-(trifluoromethyl)phenyl]-7H-thieno[2,3-b]pyridine-4,6-dione | 404 (M − 1) |
| 134 | 2,5-difluoro-3-phenyl-5-[4-(trifluoromethyl)phenyl]-7H-thieno[2,3-b]pyridine-4,6-dione | 422 (M − 1) |
| 135 | 5-fluoro-5-phenyl-3-[4-(trifluoromethyl)phenyl]-7H-thieno[2,3-b]pyridine-4,6-dione | 404 (M − 1) |
| 136 | 5-fluoro-3-(m-tolyl)-5-phenyl-7H-thieno[2,3-b]pyridine-4,6-dione | 350 (M − 1) |
| 137 | 2,5-difluoro-3-(m-tolyl)-5-phenyl-7H-thieno[2,3-b]pyridine-4,6-dione | 368 (M − 1) |
| 138 | 3-(2-chlorophenyl)-5-fluoro-5-phenyl-7H-thieno[2,3-b]pyridine-4,6-dione | 370 (M − 1) |
| 139 | 2-chloro-3-(2-fluorophenyl)-5-methyl-5-(3-methylsulfonylphenyl)-7H-thieno[2,3-b]pyridine-4,6-dione | 462 (M − 1) |
| 140 | 2-chloro-5-(4-hydroxyphenyl)-5-methyl-3-phenyl-7H-thieno[2,3-b]pyridine-4,6-dione | 384 (M + 1) |
| 141 | 2-chloro-3-(2-methoxyphenyl)-5-methyl-5-(4-methylsulfonylphenyl)-7H-thieno[2,3-b]pyridine-4,6-dione | 476 (M + 1) |
| 142 | 3-(4-tert-butylphenyl)-5-fluoro-5-phenyl-7H-thieno[2,3-b]pyridine-4,6-dione | 392 (M − 1) |
| 143 | 3-(4-tert-butylphenyl)-2-chloro-5-fluoro-5-phenyl-7H-thieno[2,3-b]pyridine-4,6-dione | 426 (M − 1) |
| 144 | 2-chloro-5-methyl-5-(m-tolyl)-3-(p-tolyl)-7H-thieno[2,3-b]pyridine-4,6-dione | 396 (M + 1) |
| 145 | 2-chloro-3-(2-methoxyphenyl)-5-methyl-5-phenyl-7H-thieno[2,3-b]pyridine-4,6-dione | 398 (M + 1) |
| 146 | 2-chloro-3-(3-fluorophenyl)-5-(4-methoxyphenyl)-5-methyl-7H-thieno[2,3-b]pyridine-4,6-dione | 416 (M + 1) |
| 147 | 5-fluoro-3-(2-hydroxyphenyl)-5-phenyl-7H-thieno[2,3-b]pyridine-4,6-dione | 352 (M − 1) |
| 148 | 2-chloro-3-(3-fluorophenyl)-5-methyl-5-(3-methylsulfonylphenyl)-7H-thieno[2,3-b]pyridine-4,6-dione | 462 (M − 1) |
| 149 | 2-chloro-3-(3-fluorophenyl)-5-methyl-5-(4-methylsulfonylphenyl)-7H-thieno[2,3-b]pyridine-4,6-dione | 462 (M − 1) |
| 150 | 2-chloro-5-(4-methoxyphenyl)-5-methyl-3-(p-tolyl)-7H-thieno[2,3-b]pyridine-4,6-dione | 412 (M + 1) |
| 151 | 3-(2-benzyloxy-5-fluoro-phenyl)-2-chloro-5-fluoro-5-phenyl-7H-thieno[2,3-b]pyridine-4,6-dione | 494.0 (M − 1) |
| 152 | 3-(2-benzyloxy-5-methoxy-phenyl)-5-fluoro-5-phenyl-7H-thieno[2,3-b]pyridine-4,6-dione | 472.0 (M − 1) |
| 153 | 2-chloro-5-(2-fluorophenyl)-3-(4-methoxyphenyl)-5-methyl-7H-thieno[2,3-b]pyridine-4,6-dione | 416.1 (M + 1) |
| 154 | 2-chloro-5-methyl-3,5-bis(p-tolyl)-7H-thieno[2,3-b]pyridine-4,6-dione | 369.2 (M + 1) |
| 155 | 2-chloro-5-(4-methoxyphenyl)-5-methyl-3-(m-tolyl)-7H-thieno[2,3-b]pyridine-4,6-dione | 412.2 (M + 1) |
| 156 | 2-chloro-5-(2-fluorophenyl)-5-methyl-3-(m-tolyl)-7H-thieno[2,3-b]pyridine-4,6-dione | 400.2 (M + 1) |
| 157 | 2-chloro-5-fluoro-3-(3-fluorophenyl)-5-phenyl-7H-thieno[2,3-b]pyridine-4,6-dione | 390 (M + 1) |
| 158 | 2-chloro-5-(3-fluorophenyl)-5-methyl-3-(m-tolyl)-7H-thieno[2,3-b]pyridine-4,6-dione | 400.2 (M + 1) |
| 159 | 3-(4-bromo-3-methoxy-phenyl)-5-fluoro-5-phenyl-7H-thieno[2,3-b]pyridine-4,6-dione | 444.1 (M − 1) |
| 160 | 3-(4-bromo-3-methoxy-phenyl)-2,5-difluoro-5-phenyl-7H-thieno[2,3-b]pyridine-4,6-dione | 462.1 (M − 1) |
| 161 | 5-fluoro-3-(2-naphthyl)-5-phenyl-7H-thieno[2,3-b]pyridine-4,6-dione | 404.2 (M − 1) |
| 162 | 2,5-difluoro-3-(2-naphthyl)-5-phenyl-7H-thieno[2,3-b]pyridine-4,6-dione | 386.2 (M − 1) |
| 163 | 3-(3-bromophenyl)-5-fluoro-5-phenyl-7H-thieno[2,3-b]pyridine-4,6-dione | 414.1 (M − 1) |
| 164 | 3-(3-bromophenyl)-2,5-difluoro-5-phenyl-7H-thieno[2,3-b]pyridine-4,6-dione | 432.0 (M − 1) |
| 165 | 2,5-difluoro-3-(4-fluorophenyl)-5-(4-methoxyphenyl)-7H-thieno[2,3-b]pyridine-4,6-dione | 402.1 (M − 1) |
| 166 | 3-(4-bromophenyl)-5-fluoro-5-(3-pyridyl)-7H-thieno[2,3-b]pyridine-4,6-dione | 415.1 (M − 1) |
| 167 | 5-fluoro-5-(4-methoxyphenyl)-3-phenyl-7H-thieno[2,3-b]pyridine-4,6-dione | 366.2 (M − 1) |
| 168 | 2,5-difluoro-5-(4-methoxyphenyl)-3-phenyl-7H-thieno[2,3-b]pyridine-4,6-dione | 384.2 (M − 1) |
| 169 | 2-chloro-5-fluoro-3-(4-fluoro-2-hydroxy-phenyl)-5-(4-methoxyphenyl)-7H-thieno[2,3-b]pyridine-4,6-dione | 433.8 (M − 1) |
| 170 | 2-chloro-5-(4-fluorophenyl)-5-methyl-3-(m-tolyl)-7H-thieno[2,3-b]pyridine-4,6-dione | 400.0 (M + 1) |
| 171 | 2-chloro-5-methyl-3,5-bis(m-tolyl)-7H-thieno[2,3-b]pyridine-4,6-dione | 396.0 (M + 1) |
| 172 | 3-(4-chlorophenyl)-5-fluoro-5-phenyl-7H-thieno[2,3-b]pyridine-4,6-dione | 369.9 (M − 1) |
| 173 | 3-(4-chlorophenyl)-2,5-difluoro-5-phenyl-7H-thieno[2,3-b]pyridine-4,6-dione | 387.8 (M − 1) |
| 174 | 3-benzyloxy-4-fluoro-phenyl)-5-fluoro-5-phenyl-7H-thieno[2,3-b]pyridine-4,6-dione | 460.2 (M − 1) |
| 175 | 3-(2-benzyloxy-4-fluoro-phenyl)-2,5-difluoro-5-phenyl-7H-thieno[2,3-b]pyridine-4,6-dione | 478.2 (M − 1) |
| 176 | 2,5-dichloro-3-(4-fluoro-2-hydroxy-phenyl)-5-(m-tolyl)-7H-thieno[2,3-b]pyridine-4,6-dione | 433.9 (M − 1) |
| 177 | 5-fluoro-3-(2-fluorophenyl)-5-phenyl-7H-thieno[2,3-b]pyridine-4,6-dione | 354.1 (M − 1) |
| 178 | 2,5-difluoro-3-(2-fluorophenyl)-5-phenyl-7H-thieno[2,3-b]pyridine-4,6-dione | 372.1 (M − 1) |

TABLE (1)-continued

| No | name | MS |
|---|---|---|
| 179 | 3-(2,4-difluorophenyl)-5-fluoro-5-phenyl-7H-thieno[2,3-b]pyridine-4,6-dione | 371.9 (M − 1) |
| 180 | 5-fluoro-3-(2-methoxyphenyl)-5-phenyl-7H-thieno[2,3-b]pyridine-4,6-dione | 365.9 (M − 1) |
| 181 | 2,5-difluoro-3-(2-methoxyphenyl)-5-phenyl-7H-thieno[2,3-b]pyridine-4,6-dione | 383.9 (M − 1) |
| 182 | 5-fluoro-5-(3-methoxyphenyl)-3-phenyl-7H-thieno[2,3-b]pyridine-4,6-dione | 366.2 (M − 1) |
| 183 | 2,5-difluoro-5-(3-methoxyphenyl)-3-phenyl-7H-thieno[2,3-b]pyridine-4,6-dione | 384.2 (M − 1) |
| 184 | 2-chloro-5-fluoro-3-(4-fluoro-2-hydroxy-phenyl)-5-(m-tolyl)-7H-thieno[2,3-b]pyridine-4,6-dione | 417.9 (M − 1) |
| 185 | 2-chloro-5-fluoro-3-(4-fluoro-2-hydroxy-3-methyl-phenyl)-5-phenyl-7H-thieno[2,3-b]pyridine-4,6-dione | 417.9 (M − 1) |
| 186 | 2-chloro-3-(3,4-dimethylphenyl)-5-fluoro-5-(m-tolyl)-7H-thieno[2,3-b]pyridine-4,6-dione | 414.0 (M + 1) |
| 187 | 2-chloro-3-(3,4-dimethylphenyl)-5-fluoro-5-(3-pyridyl)-7H-thieno[2,3-b]pyridine-4,6-dione | 401.0 (M + 1) |
| 188 | 3-(4-bromophenyl)-5-fluoro-5-(2-pyridyl)-7H-thieno[2,3-b]pyridine-4,6-dione | 414.8 (M − 1) |
| 189 | 5-fluoro-3-(4-fluorophenyl)-5-phenyl-7H-thieno[2,3-b]pyridine-4,6-dione | 353.9 (M − 1) |
| 190 | 5-fluoro-3-(3-fluorophenyl)-5-phenyl-7H-thieno[2,3-b]pyridine-4,6-dione | 353.9 (M − 1) |
| 191 | 2-chloro-5-fluoro-3-(3-fluoro-2-hydroxy-4-methyl-phenyl)-5-phenyl-7H-thieno[2,3-b]pyridine-4,6-dione | 417.9 (M − 1) |
| 192 | 5-fluoro-3-(3-fluoro-2-hydroxy-4-methyl-phenyl)-2-methyl-5-phenyl-7H-thieno[2,3-b]pyridine-4,6-dione | 397.9 (M − 1) |
| 193 | 5-fluoro-5-phenyl-3-pyrazin-2-yl-7H-thieno[2,3-b]pyridine-4,6-dione | 340.0 (M + 1) |
| 194 | 5-fluoro-3-(3-fluoro-4-hydroxy-phenyl)-5-phenyl-7H-thieno[2,3-b]pyridine-4,6-dione | 369.9 (M − 1) |
| 195 | 2,5-difluoro-3-(3-fluoro-4-methoxy-phenyl)-5-phenyl-7H-thieno[2,3-b]pyridine-4,6-dione | 401.9 (M − 1) |
| 196 | 3-(5-fluoro-4,6-dioxo-5-phenyl-7H-thieno[2,3-b]pyridin-3-yl)benzoic acid | 379.9 (M − 1) |
| 197 | 3-(2,5-difluoro-4,6-dioxo-5-phenyl-7H-thieno[2,3-b]pyridin-3-yl)benzoic acid | 397.9 (M − 1) |
| 198 | 4-(5-fluoro-4,6-dioxo-5-phenyl-7H-thieno[2,3-b]pyridin-3-yl)benzoic acid | 379.9 (M − 1) |
| 199 | 5-fluoro-5-(4-fluorophenyl)-3-(4-methoxyphenyl)-7H-thieno[2,3-b]pyridine-4,6-dione | 384.1 (M − 1) |
| 200 | 2,5-difluoro-5-(4-fluorophenyl)-3-(4-methoxyphenyl)-7H-thieno[2,3-b]pyridine-4,6-dione | 402.1 (M − 1) |
| 201 | 5-fluoro-3-(4-methoxyphenyl)-5-phenyl-7H-thieno[2,3-b]pyridine-4,6-dione | 365.9 (M − 1) |
| 202 | 2,5-difluoro-3-(4-methoxyphenyl)-5-phenyl-7H-thieno[2,3-b]pyridine-4,6-dione | 383.9 (M − 1) |
| 203 | 5-fluoro-3-(4-hydroxyphenyl)-5-phenyl-7H-thieno[2,3-b]pyridine-4,6-dione | 351.9 (M − 1) |
| 204 | 5-fluoro-3-(3-hydroxyphenyl)-5-phenyl-7H-thieno[2,3-b]pyridine-4,6-dione | 351.9 (M − 1) |
| 205 | 5-fluoro-3-(3-methoxyphenyl)-5-phenyl-7H-thieno[2,3-b]pyridine-4,6-dione | 365.9 (M − 1) |
| 206 | 2,5-difluoro-3-(3-methoxyphenyl)-5-phenyl-7H-thieno[2,3-b]pyridine-4,6-dione | 383.9 (M − 1) |
| 207 | 5-fluoro-5-(2-methoxyphenyl)-3-phenyl-7H-thieno[2,3-b]pyridine-4,6-dione | 365.9 (M − 1) |
| 208 | 5-fluoro-5-phenyl-3-(4-pyridyl)-7H-thieno[2,3-b]pyridine-4,6-dione | 336.9 (M − 1) |
| 209 | 2-chloro-5-(3-methoxyphenyl)-5-methyl-3-(p-tolyl)-7H-thieno[2,3-b]pyridine-4,6-dione | 300.1 (M + 1) |
| 210 | 2-chloro-5-fluoro-3-(3-fluorophenyl)-5-(m-tolyl)-7H-thieno[2,3-b]pyridine-4,6-dione | 401.9 (M − 1) |
| 211 | 3-[2-chloro-5-fluoro-3-(3-fluorophenyl)-4,6-dioxo-7H-thieno[2,3-b]pyridin-5-yl]benzonitrile | 412.8 (M − 1) |
| 212 | 2-chloro-5-fluoro-3-(3-fluorophenyl)-5-(3-pyridyl)-7H-thieno[2,3-b]pyridine-4,6-dione | 391.0 (M + 1) |
| 213 | 2-chloro-5-fluoro-3-(2-hydroxy-3-methyl-phenyl)-5-phenyl-7H-thieno[2,3-b]pyridine-4,6-dione | 399.9 (M − 1) |
| 214 | 5-fluoro-5-phenyl-3-(3-pyridyl)-7H-thieno[2,3-b]pyridine-4,6-dione | 337.0 (M − 1) |
| 215 | 2-chloro-5-fluoro-3-(4-fluoro-2-hydroxy-phenyl)-5-(3-fluorophenyl)-7H-thieno[2,3-b]pyridine-4,6-dione | 421.9 (M − 1) |
| 216 | 2,5-dichloro-3-(4-fluoro-2-hydroxy-phenyl)-5-phenyl-7H-thieno[2,3-b]pyridine-4,6-dione | 419.8 (M − 1) |
| 217 | 3-[2-chloro-3-(3,4-dimethylphenyl)-5-fluoro-4,6-dioxo-7H-thieno[2,3-b]pyridin-5-yl]benzonitrile | 422.9 (M − 1) |
| 218 | 2-chloro-5-fluoro-3-(4-fluoro-2-hydroxy-phenyl)-5-(4-methylsulfonylphenyl)-7H-thieno[2,3-b]pyridine-4,6-dione | 481.8 (M − 1) |
| 219 | 2-chloro-5-(3,4-dimethoxyphenyl)-5-fluoro-3-(4-fluoro-2-hydroxy-phenyl)-7H-thieno[2,3-b]pyridine-4,6-dione | 463.9 (M − 1) |
| 220 | 5-fluoro-3-(4-fluoro-2-hydroxy-phenyl)-2-methyl-5-phenyl-7H-thieno[2,3-b]pyridine-4,6-dione | 384.0 (M − 1) |
| 221 | 2-chloro-5-fluoro-3-(5-fluoro-2-hydroxy-phenyl)-5-phenyl-7H-thieno[2,3-b]pyridine-4,6-dione | 388 (M + 1) |
| 222 | 2,5-dichloro-3,5-diphenyl-7H-thieno[2,3-b]pyridine-4,6-dione | 385.9 (M − 1) |
| 223 | 2-chloro-3-(4-ethyl-2-hydroxy-phenyl)-5-fluoro-5-phenyl-7H-thieno[2,3-b]pyridine-4,6-dione | 413.9 (M − 1) |
| 224 | 3-[2-chloro-5-fluoro-3-(4-fluoro-2-hydroxy-phenyl)-4,6-dioxo-7H-thieno[2,3-b]pyridin-5-yl]benzonitrile | 428.9 (M − 1) |
| 225 | 2-chloro-5-fluoro-3-(4-fluoro-2-hydroxy-phenyl)-5-(4-methoxy-3-methyl-phenyl)-7H-thieno[2,3-b]pyridine-4,6-dione | 447.9 (M − 1) |
| 226 | 2-chloro-5-fluoro-3-(4-fluoro-2-hydroxy-phenyl)-5-(3-thienyl)-7H-thieno[2,3-b]pyridine-4,6-dione | 409.9 (M − 1) |
| 227 | 2-chloro-5-fluoro-3-(3-fluoro-2-methoxy-4-methyl-phenyl)-5-(4-fluorophenyl)-7H-thieno[2,3-b]pyridine-4,6-dione | 449.9 (M − 1) |
| 228 | 2-chloro-5-fluoro-3-(3-fluoro-2-hydroxy-4-methyl-phenyl)-5-(4-fluorophenyl)-7H-thieno[2,3-b]pyridine-4,6-dione | 435.9 (M − 1) |
| 229 | 2-chloro-5-fluoro-3-(4-fluoro-2-methoxy-3-methyl-phenyl)-5-phenyl-7H-thieno[2,3-b]pyridine-4,6-dione | 432.0 (M − 1) |
| 230 | 2-chloro-5-fluoro-3-(3-fluoro-2-methoxy-4-methyl-phenyl)-5-phenyl-7H-thieno[2,3-b]pyridine-4,6-dione | 431.9 (M − 1) |
| 231 | 2-chloro-3-(4-fluoro-2-hydroxy-phenyl)-5-methoxy-5-phenyl-7H-thieno[2,3-b]pyridine-4,6-dione | 418 (M + 1) |
| 232 | 2,5-dichloro-3-(3-fluoro-2-hydroxy-4-methyl-phenyl)-5-phenyl-7H-thieno[2,3-b]pyridine-4,6-dione | 433.9 (M − 1) |
| 233 | 2,5-dichloro-3-(4-fluoro-2-hydroxy-3-methyl-phenyl)-5-phenyl-7H-thieno[2,3-b]pyridine-4,6-dione | 433.9 (M − 1) |

BIOLOGICAL ASSAYS

Enzymatic Activity

The following biological test allows the determination of the efficacy of compounds of formula (1) onto AMPK protein.

AMPK enzyme activities were assayed by using a Delfia technology. AMPK enzyme activities were carried out in microtiter plates in the presence of a synthetic peptide substrate (AMARAASAAALARRR, the "AMARA" peptide) and activators in serial dilutions. Reactions were initiated by the addition of AMPK. Enzyme activity was assayed by using an anti-phosphoserine antibody to measure the quantity of phosphate incorporated into the AMARAA.

No: Number of the molecule

Activity: Ratio between the % of control (basal activity) of compound of formula (1) at 30 μM and the % of control (basal activity) of AMP (natural substrate) at 200 μM.

0%<A<50%, 50%≤B<75%, C≥75%

The results are presented in table 2 below.

TABLE (2)

| No | activity |
|---|---|
| 1 | A |
| 2 | B |
| 3 | C |
| 4 | A |
| 5 | A |
| 6 | A |
| 7 | A |
| 8 | A |
| 9 | A |
| 10 | A |

TABLE (2)-continued

| No | activity |
|---|---|
| 11 | A |
| 12 | A |
| 13 | A |
| 14 | A |
| 15 | A |
| 16 | A |
| 17 | A |
| 18 | A |
| 19 | A |
| 20 | C |
| 21 | A |
| 22 | B |
| 23 | A |
| 24 | A |
| 25 | C |
| 26 | A |
| 27 | A |
| 28 | A |
| 29 | C |
| 30 | A |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | B |
| 47 | A |
| 48 | A |
| 49 | A |
| 50 | A |
| 51 | A |
| 52 | A |
| 53 | A |
| 54 | A |
| 55 | B |
| 56 | A |
| 57 | B |
| 58 | C |
| 59 | C |
| 60 | C |
| 61 | C |
| 62 | C |
| 63 | C |
| 64 | C |
| 65 | C |
| 66 | C |
| 67 | C |
| 68 | C |
| 69 | C |
| 70 | C |
| 71 | B |
| 72 | C |
| 73 | C |
| 74 | C |
| 75 | A |
| 76 | A |
| 77 | B |
| 78 | A |
| 79 | C |
| 80 | C |
| 81 | B |
| 82 | A |
| 83 | A |
| 84 | B |
| 85 | A |
| 86 | A |
| 87 | A |
| 88 | A |
| 89 | A |
| 90 | A |
| 91 | A |
| 92 | A |
| 93 | A |
| 94 | C |
| 95 | B |
| 96 | A |
| 97 | C |
| 98 | A |
| 99 | C |
| 100 | B |
| 101 | B |
| 102 | C |
| 103 | A |
| 104 | B |
| 105 | A |
| 106 | A |
| 107 | A |
| 108 | C |
| 109 | C |
| 110 | C |
| 111 | C |
| 112 | A |
| 113 | B |
| 114 | B |
| 115 | C |
| 116 | C |
| 117 | A |
| 118 | B |
| 119 | B |
| 120 | A |
| 121 | C |
| 122 | C |
| 123 | C |
| 124 | B |
| 125 | A |
| 126 | B |
| 127 | A |
| 128 | A |
| 129 | B |
| 130 | B |
| 131 | B |
| 132 | A |
| 133 | A |
| 134 | A |
| 135 | A |
| 136 | B |
| 137 | C |
| 138 | B |
| 139 | A |
| 140 | A |
| 141 | A |
| 142 | A |
| 143 | A |
| 144 | A |
| 145 | A |
| 146 | A |
| 147 | C |
| 148 | A |
| 149 | A |
| 150 | A |
| 151 | A |
| 152 | B |
| 153 | A |
| 154 | A |
| 155 | A |
| 156 | A |
| 157 | C |
| 158 | A |
| 159 | C |
| 160 | B |
| 161 | C |
| 162 | C |
| 163 | B |
| 164 | C |
| 165 | C |
| 166 | A |

TABLE (2)-continued

| No | activity |
|---|---|
| 167 | A |
| 168 | A |
| 169 | C |
| 170 | A |
| 171 | A |
| 172 | B |
| 173 | B |
| 174 | A |
| 175 | A |
| 176 | C |
| 177 | A |
| 178 | B |
| 179 | A |
| 180 | A |
| 181 | A |
| 182 | C |
| 183 | B |
| 184 | C |
| 185 | C |
| 186 | C |
| 187 | C |
| 188 | A |
| 189 | A |
| 190 | B |
| 191 | C |
| 192 | C |
| 193 | A |
| 194 | C |
| 195 | C |
| 196 | A |
| 197 | A |
| 198 | A |
| 199 | B |
| 200 | B |
| 201 | B |
| 202 | B |
| 203 | C |
| 204 | C |
| 205 | B |
| 206 | C |
| 207 | A |
| 208 | A |
| 209 | A |
| 210 | C |
| 211 | C |
| 212 | C |
| 213 | C |
| 214 | A |
| 215 | C |
| 216 | C |
| 217 | C |
| 218 | C |
| 219 | C |
| 220 | B |
| 221 | C |
| 222 | C |
| 223 | C |
| 224 | C |
| 225 | C |
| 226 | C |
| 227 | B |
| 228 | C |
| 229 | A |
| 230 | A |
| 231 | C |
| 232 | C |
| 233 | C |

The invention claimed is:

1. A compound of formula (1)

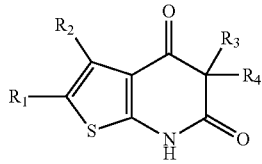

or a pharmaceutically acceptable salt thereof wherein
$R_1$ represents a hydrogen atom, an alkyl group or a halogen atom;
$R_2$ represents an optionally substituted aryl or optionally substituted heteroaryl group;
$R_3$ is phenyl optionally substituted with by one or more of halogen, alkyl, hydroxyl, alkoxy, aralkyloxy, amino, mono- or di-alkylamino, carboxy, alkyloxycarbonyl, mono- or di-alkylaminocarbonyl, carboxamide, cyano, alkylsulfonyl or trifluoromethyl groups; and
$R_4$ is fluoro
wherein said aryl or heteroaryl are optionally substituted by one or more atoms or groups selected from the group consisting of halogen atoms, alkyl groups, hydroxyl groups, alkoxy groups, aralkyloxy groups, amino, mono- or di-alkylamino groups, carboxy groups, alkyloxycarbonyl groups, mono- or di-alkylaminocarbonyl groups, carboxamide, cyano, alkylsulfonyl and trifluoromethyl groups.

2. The compound according to claim 1, wherein $R_2$ represents an aryl group.

3. The compound according to claim 1, wherein $R_1$ represents an alkyl group.

4. The compound according to claim 1, wherein $R_1$ represents a halogen atom.

5. The compound according to claim 1, selected from the group consisting of:
2-chloro-5-fluoro-3,5-diphenyl-7H-thieno[2,3-b]pyridine-4,6-dione
5-fluoro-3-(4-fluoro-2-hydroxy-phenyl)-5-phenyl-7H-thieno[2,3-b]pyridine-4,6-dione
2-chloro-5-fluoro-3-(4-fluoro-2-hydroxy-phenyl)-5-phenyl-7H-thieno[2,3-b]pyridine-4,6-dione
5-fluoro-2-methyl-3,5-diphenyl-7H-thieno[2,3-b]pyridine-4,6-dione
2-chloro-5-fluoro-5-phenyl-3-(3-pyridyl)-7H-thieno[2,3-b]pyridine-4,6-dione
2-chloro-5-fluoro-3-(4-hydroxyphenyl)-5-phenyl-7H-thieno[2,3-b]pyridine-4,6-dione
2-chloro-5-fluoro-3-(2-fluorophenyl)-5-phenyl-7H-thieno[2,3-b]pyridine-4,6-dione
2-chloro-5-fluoro-3-(2-fluoro-4-methoxy-phenyl)-5-phenyl-7H-thieno[2,3-b]pyridine-4,6-dione
2-chloro-5-fluoro-3-(3-fluoro-4-hydroxy-phenyl)-5-phenyl-7H-thieno[2,3-b]pyridine-4,6-dione
5-fluoro-5-(2-methoxyphenyl)-2-methyl-3-phenyl-7H-thieno[2,3-b]pyridine-4,6-dione
2-chloro-5-fluoro-3-(m-tolyl)-5-phenyl-7H-thieno[2,3-b]pyridine-4,6-dione
2-chloro-5-fluoro-5-phenyl-3-(p-tolyl)-7H-thieno[2,3-b]pyridine-4,6-dione
2-chloro-5-fluoro-3-(4-methoxyphenyl)-5-phenyl-7H-thieno[2,3-b]pyridine-4,6-dione 2-chloro-5-fluoro-5-(3-methylsulfonylphenyl)-3-phenyl-7H-thieno[2,3-b]pyridine-4,6-dione
2-chloro-5-fluoro-5-phenyl-3-(4-pyridyl)-7H-thieno[2,3-b]pyridine-4,6-dione
2-chloro-5-fluoro-3-(3-methoxyphenyl)-5-phenyl-7H-thieno[2,3-b]pyridine-4,6-dione
2-chloro-5-fluoro-3-phenyl-5-[3-(trifluoromethyl)phenyl]-7H-thieno[2,3-b]pyridine-4,6-dione
2-chloro-5-fluoro-5-(4-methylsulfonylpheny)-3-phenyl-7H-thieno[2,3-b]pyridine-4,6-dione
2-chloro-5-fluoro-3-(2-methoxyphenyl)-5-phenyl-7H-thieno[2,3-b]pyridine-4,6-dione
2-chloro-5-fluoro-3-(4-fluoro-2-hydroxy-phenyl)-5-(2-methoxyphenyl)-7H-thieno[2,3-b]pyridine-4,6-dione
5-fluoro-3,5-diphenyl-7H-thieno[2,3-b]pyridine-4,6-dione
2-chloro-3-(2-chlorophenyl)-5-fluoro-5-phenyl-7H-thieno[2,3-b]pyridine-4,6-dione
5-fluoro-3-(4-fluoro-2-hydroxy-3-methyl-phenyl)-5-phenyl-7H-thieno[2,3-b]pyridine-4,6-dione
5-fluoro-3-(4-fluoro-2-hydroxy-3-methyl-phenyl)-5-(4-fluorophenyl)-7H-thieno[2,3-b]pyridine-4,6-dione
5-fluoro-3-(4-fluoro-2-hydroxy-phenyl)-5-(p-tolyl)-7H-thieno[2,3-b]pyridine-4,6-dione
3-[5-fluoro-3-(2-methoxy-4-methyl-phenyl)-4,6-dioxo-7H-thieno[2,3-b]pyridin-5-yl]benzonitrile
5-fluoro-3-(2-hydroxy-6-methoxy-phenyl)-5-phenyl-7H-thieno[2,3-b]pyridine-4,6-dione
5-fluoro-3-(3-methoxy-4-methyl-phenyl)-5-phenyl-7H-thieno[2,3-b]pyridine-4,6-dione
2,5-difluoro-3-(3-methoxy-4-methyl-phenyl)-5-phenyl-7H-thieno[2,3-b]pyridine-4,6-dione
5-fluoro-3-(3-hydroxy-4-methyl-phenyl)-5-phenyl-7H-thieno[2,3-b]pyridine-4,6-dione
2,5-difluoro-3-(3-hydroxy-4-methyl-phenyl)-5-phenyl-7H-thieno[2,3-b]pyridine-4,6-dione
5-fluoro-3-(2-methoxy-4-methyl-phenyl)-5-phenyl-7H-thieno[2,3-b]pyridine-4,6-dione
2,5-difluoro-3-(2-methoxy-4-methyl-phenyl)-5-phenyl-7H-thieno[2,3-b]pyridine-4,6-dione
5-fluoro-3-(3-methylsulfonylphenyl)-5-phenyl-7H-thieno[2,3-b]pyridine-4,6-dione
5-fluoro-3-(2-hydroxy-4-methyl-phenyl)-5-phenyl-7H-thieno[2,3-b]pyridine-4,6-dione
3-(2,6-difluorophenyl)-5-fluoro-5-phenyl-7H-thieno[2,3-b]pyridine-4,6-dione
3-(4-bromo-2-hydroxy-phenyl)-5-fluoro-5-phenyl-7H-thieno[2,3-b]pyridine-4,6-dione
3-(4-bromophenyl)-5-fluoro-5-(4-pyridyl)-7H-thieno[2,3-b]pyridine-4,6-dione
3-(2-bromophenyl)-5-fluoro-5-phenyl-7H-thieno[2,3-b]pyridine-4,6-dione
3-(4-bromo-2-methoxy-phenyl)-5-fluoro-5-phenyl-7H-thieno[2,3-b]pyridine-4,6-dione
3-(4-bromo-2-methoxy-phenyl)-2,5-difluoro-5-phenyl-7H-thieno[2,3-b]pyridine-4,6-dione
5-fluoro-3-(o-tolyl)-5-phenyl-7H-thieno[2,3-b]pyridine-4,6-dione
2,5-difluoro-3-(o-tolyl)-5-phenyl-7H-thieno[2,3-b]pyridine-4,6-dione
5-fluoro-3-phenyl-5-[3-(trifluoromethyl)phenyl]-7H-thieno[2,3-b]pyridine-4,6-dione
2,5-difluoro-3-phenyl-5-[3-(trifluoromethyl)phenyl]-7H-thieno[2,3-b]pyridine-4,6-dione
5-fluoro-3-phenyl-5-[4-(trifluoromethyl)phenyl]-7H-thieno[2,3-b]pyridine-4,6-dione
2,5-difluoro-3-phenyl-5-[4-(trifluoromethyl)phenyl]-7H-thieno[2,3-b]pyridine-4,6-dione
5-fluoro-5-phenyl-3-[4-(trifluoromethyl)phenyl]-7H-thieno[2,3-b]pyridine-4,6-dione
5-fluoro-3-(m-tolyl)-5-phenyl-7H-thieno[2,3-b]pyridine-4,6-dione
2,5-difluoro-3-(m-tolyl)-5-phenyl-7H-thieno[2,3-b]pyridine-4,6-dione
3-(2-chlorophenyl)-5-fluoro-5-phenyl-7H-thieno[2,3-b]pyridine-4,6-dione
3-(4-tert-butylphenyl)-5-fluoro-5-phenyl-7H-thieno[2,3-b]pyridine-4,6-dione
3-(4-tert-butylphenyl)-2-chloro-5-fluoro-5-phenyl-7H-thieno[2,3-b]pyridine-4,6-dione
5-fluoro-3-(2-hydroxyphenyl)-5-phenyl-7H-thieno[2,3-b]pyridine-4,6-dione
3-(2-benzyloxy-5-fluoro-phenyl)-2-chloro-5-fluoro-5-phenyl-7H-thieno[2,3-b]pyridine-4,6-dione
3-(2-benzyloxy-5-methoxy-phenyl)-5-fluoro-5-phenyl-7H-thieno[2,3-b]pyridine-4,6-dione
2-chloro-5-fluoro-3-(3-fluorophenyl)-5-phenyl-7H-thieno[2,3-b]pyridine-4,6-dione
3-(4-bromo-3-methoxy-phenyl)-5-fluoro-5-phenyl-7H-thieno[2,3-b]pyridine-4,6-dione
3-(4-bromo-3-methoxy-phenyl)-2,5-difluoro-5-phenyl-7H-thieno[2,3-b]pyridine-4,6-dione
5-fluoro-3-(2-naphthyl)-5-phenyl-7H-thieno[2,3-b]pyridine-4,6-dione
2,5-difluoro-3-(2-naphthyl)-5-phenyl-7H-thieno[2,3-b]pyridine-4,6-dione
3-(3-bromophenyl)-5-fluoro-5-phenyl-7H-thieno[2,3-b]pyridine-4,6-dione
3-(3-bromophenyl)-2,5-difluoro-5-phenyl-7H-thieno[2,3-b]pyridine-4,6-dione
2,5-difluoro-3-(4-fluorophenyl)-5-(4-methoxyphenyl)-7H-thieno[2,3-b]pyridine-4,6-dione
3-(4-bromophenyl)-5-fluoro-5-(3-pyridyl)-7H-thieno[2,3-b]pyridine-4,6-dione
5-fluoro-5-(4-methoxyphenyl)-3-phenyl-7H-thieno[2,3-b]pyridine-4,6-dione
2,5-difluoro-5-(4-methoxyphenyl)-3-phenyl-7H-thieno[2,3-b]pyridine-4,6-dione
2-chloro-5-fluoro-3-(4-fluoro-2-hydroxy-phenyl)-5-(4-methoxyphenyl)-7H-thieno[2,3-b]pyridine-4,6-dione
3-(4-chlorophenyl)-5-fluoro-5-phenyl-7H-thieno[2,3-b]pyridine-4,6-dione
3-(4-chlorophenyl)-2,5-difluoro-5-phenyl-7H-thieno[2,3-b]pyridine-4,6-dione
3-(2-benzyloxy-4-fluoro-phenyl)-5-fluoro-5-phenyl-7H-thieno[2,3-b]pyridine-4,6-dione
3-(2-benzyloxy-4-fluoro-phenyl)-2,5-difluoro-5-phenyl-7H-thieno[2,3-b]pyridine-4,6-dione
5-fluoro-3-(2-fluorophenyl)-5-phenyl-7H-thieno[2,3-b]pyridine-4,6-dione
2,5-difluoro-3-(2-fluorophenyl)-5-phenyl-7H-thieno[2,3-b]pyridine-4,6-dione
3-(2,4-difluorophenyl)-5-fluoro-5-phenyl-7H-thieno[2,3-b]pyridine-4,6-dione
5-fluoro-3-(2-methoxyphenyl)-5-phenyl-7H-thieno[2,3-b]pyridine-4,6-dione
2,5-difluoro-3-(2-methoxyphenyl)-5-phenyl-7H-thieno[2,3-b]pyridine-4,6-dione
5-fluoro-5-(3-methoxyphenyl)-3-phenyl-7H-thieno[2,3-b]pyridine-4,6-dione
2,5-difluoro-5-(3-methoxyphenyl)-3-phenyl-7H-thieno[2,3-b]pyridine-4,6-dione 2-chloro-5-fluoro-3-(4-fluoro-2-hydroxy-phenyl)-5-(m-tolyl)-7H-thieno[2,3-b]pyridine-4,6-dione
2-chloro-5-fluoro-3-(4-fluoro-2-hydroxy-3-methyl-phenyl)-5-phenyl-7H-thieno[2,3-b]pyridine-4,6-dione
2-chloro-3-(3,4-dimethylphenyl)-5-fluoro-5-(m-tolyl)-7H-thieno[2,3-b]pyridine-4,6-dione
2-chloro-3-(3,4-dimethylphenyl)-5-fluoro-5-(3-pyridyl)-7H-thieno[2,3-b]pyridine-4,6-dione
3-(4-bromophenyl)-5-fluoro-5-(2-pyridyl)-7H-thieno[2,3-b]pyridine-4,6-dione
5-fluoro-3-(4-fluorophenyl)-5-phenyl-7H-thieno[2,3-b]pyridine-4,6-dione
5-fluoro-3-(3-fluorophenyl)-5-phenyl-7H-thieno[2,3-b]pyridine-4,6-dione
2-chloro-5-fluoro-3-(3-fluoro-2-hydroxy-4-methyl-phenyl)-5-phenyl-7H-thieno[2,3-b]pyridine-4,6-dione
5-fluoro-3-(3-fluoro-2-hydroxy-4-methyl-phenyl)-2-methyl-5-phenyl-7H-thieno[2,3-b]pyridine-4,6-dione
5-fluoro-5-phenyl-3-pyrazin-2-yl-7H-thieno[2,3-b]pyridine-4,6-dione
5-fluoro-3-(3-fluoro-4-hydroxy-phenyl)-5-phenyl-7H-thieno[2,3-b]pyridine-4,6-dione
2,5-difluoro-3-(3-fluoro-4-methoxy-phenyl)-5-phenyl-7H-thieno[2,3-b]pyridine-4,6-dione
3-(5-fluoro-4,6-dioxo-5-phenyl-7H-thieno[2,3-b]pyridin-3-yl)benzoic acid
3-(2,5-difluoro-4,6-dioxo-5-phenyl-7H-thieno[2,3-b]pyridin-3-yl)benzoic acid
4-(5-fluoro-4,6-dioxo-5-phenyl-7H-thieno[2,3-b]pyridin-3-yl)benzoic acid
5-fluoro-5-(4-fluorophenyl)-3-(4-methoxyphenyl)-7H-thieno[2,3-b]pyridine-4,6-dione
2,5-difluoro-5-(4-fluorophenyl)-3-(4-methoxyphenyl)-7H-thieno[2,3-b]pyridine-4,6-dione
5-fluoro-3-(4-methoxyphenyl)-5-phenyl-7H-thieno[2,3-b]pyridine-4,6-dione
2,5-difluoro-3-(4-methoxyphenyl)-5-phenyl-7H-thieno[2,3-b]pyridine-4,6-dione
5-fluoro-3-(4-hydroxyphenyl)-5-phenyl-7H-thieno[2,3-b]pyridine-4,6-dione
5-fluoro-3-(3-hydroxyphenyl)-5-phenyl-7H-thieno[2,3-b]pyridine-4,6-dione
5-fluoro-3-(3-methoxyphenyl)-5-phenyl-7H-thieno[2,3-b]pyridine-4,6-dione
2,5-difluoro-3-(3-methoxyphenyl)-5-phenyl-7H-thieno[2,3-b]pyridine-4,6-dione
5-fluoro-5-(2-methoxyphenyl)-3-phenyl-7H-thieno[2,3-b]pyridine-4,6-dione
5-fluoro-5-phenyl-3-(4-pyridyl)-7H-thieno[2,3-b]pyridine-4,6-dione
2-chloro-5-fluoro-3-(3-fluorophenyl)-5-(m-tolyl)-7H-thieno[2,3-b]pyridine-4,6-dione
3-[2-chloro-5-fluoro-3-(3-fluorophenyl)-4,6-dioxo-7H-thieno[2,3-b]pyridin-5-yl]benzonitrile
2-chloro-5-fluoro-3-(3-fluorophenyl)-5-(3-pyridyl)-7H-thieno[2,3-b]pyridine-4,6-dione
2-chloro-5-fluoro-3-(2-hydroxy-3-methyl-phenyl)-5-phenyl-7H-thieno[2,3-b]pyridine-4,6-dione
5-fluoro-5-phenyl-3-(3-pyridyl)-7H-thieno[2,3-b]pyridine-4,6-dione
2-chloro-5-fluoro-3-(4-fluoro-2-hydroxy-phenyl)-5-(3-fluorophenyl)-7H-thieno[2,3-b]pyridine-4,6-dione
3-[2-chloro-3-(3,4-dimethylphenyl)-5-fluoro-4,6-dioxo-7H-thieno[2,3-b]pyridin-5-yl]benzonitrile
2-chloro-5-fluoro-3-(4-fluoro-2-hydroxy-phenyl)-5-(4-methylsulfonylphenyl)-7H-thieno[2,3-b]pyridine-4,6-dione
2-chloro-5-(3,4-dimethoxyphenyl)-5-fluoro-3-(4-fluoro-2-hydroxy-phenyl)-7H-thieno[2,3-b]pyridine-4,6-dione
5-fluoro-3-(4-fluoro-2-hydroxy-phenyl)-2-methyl-5-phenyl-7H-thieno[2,3-b]pyridine-4,6-dione
2-chloro-5-fluoro-3-(5-fluoro-2-hydroxy-phenyl)-5-phenyl-7H-thieno[2,3-b]pyridine-4,6-dione
2-chloro-3-(4-ethyl-2-hydroxy-phenyl)-5-fluoro-5-phenyl-7H-thieno[2,3-b]pyridine-4,6-dione
3-[2-chloro-5-fluoro-3-(4-fluoro-2-hydroxy-phenyl)-4,6-dioxo-7H-thieno[2,3-b]pyridin-5-yl]benzonitrile
2-chloro-5-fluoro-3-(4-fluoro-2-hydroxy-phenyl)-5-(4-methoxy-3-methyl-phenyl)-7H-thieno[2,3-b]pyridine-4,6-dione
2-chloro-5-fluoro-3-(4-fluoro-2-hydroxy-phenyl)-5-(3-thienyl)-7H-thieno[2,3-b]pyridine-4,6-dione
2-chloro-5-fluoro-3-(3-fluoro-2-methoxy-4-methyl-phenyl)-5-(4-fluorophenyl)-7H-thieno[2,3-b]pyridine-4,6-dione
2-chloro-5-fluoro-3-(3-fluoro-2-hydroxy-4-methyl-phenyl)-5-(4-fluorophenyl)-7H-thieno[2,3-b]pyridine-4,6-dione
2-chloro-5-fluoro-3-(4-fluoro-2-methoxy-3-methyl-phenyl)-5-phenyl-7H-thieno[2,3-b]pyridine-4,6-dione and
2-chloro-5-fluoro-3-(3-fluoro-2-methoxy-4-methyl-phenyl)-5-phenyl-7H-thieno[2,3-b]pyridine-4,6-dione.

6. A pharmaceutical composition comprising at least one compound according to claim 1 in a pharmaceutically acceptable support.

7. The compound according to claim 3, wherein $R_1$ represents a methyl group.

8. A compound according to claim 1, wherein $R_2$ represents phenyl optionally substituted with by one or more atoms of halogen, alkyl, hydroxyl, alkoxy, aralkyloxy, amino, mono- or di-alkylamino, carboxy, alkyloxycarbonyl, mono- or di-alkylaminocarbonyl, carboxamide, cyano, alkylsulfonyl or trifluoromethyl.

9. A compound according to claim 1, wherein $R_2$ represents a group of the formula:

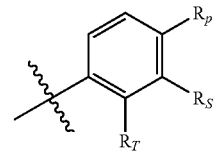

wherein
$R_p$ represents hydrogen, halogen, or alkyl;
$R_S$ represents hydrogen, halogen, or alkyl; and
$R_T$ represents hydrogen, halogen, or hydroxyl.

10. A compound according to claim 8, wherein $R_S$ is methyl or fluoro.

11. A compound according to claim 9, wherein $R_p$ is fluoro.

12. A compound according to claim 10, wherein $R_1$ is chloro.

13. A compound according to claim 1, which is 2-chloro-5-fluoro-3-(4-fluoro-2-hydroxy-3-methyl-phenyl)-5-phenyl-7H-thieno[2,3-b]pyridine-4,6-dione.

* * * * *